United States Patent [19]

Iwamoto

[11] Patent Number: 5,011,276
[45] Date of Patent: Apr. 30, 1991

[54] APPARATUS FOR MEASURING REFRACTIVE POWER OF EYE

[75] Inventor: Masakatsu Iwamoto, Kagawa, Japan

[73] Assignee: Ryusyo Industrial Co., Ltd., Osaka, Japan

[21] Appl. No.: 371,544

[22] Filed: Jun. 26, 1989

[30] Foreign Application Priority Data

| Jun. 27, 1988 | [JP] | Japan | 63-158495 |
| Dec. 29, 1988 | [JP] | Japan | 63-331999 |
| Dec. 29, 1988 | [JP] | Japan | 63-332000 |
| May 29, 1989 | [JP] | Japan | 1-136389 |
| May 29, 1989 | [JP] | Japan | 1-136390 |

[51] Int. Cl.⁵ .............................................. A61B 3/10
[52] U.S. Cl. ..................................... 351/211; 351/208
[58] Field of Search ................ 351/205, 206, 211, 208

[56] References Cited

U.S. PATENT DOCUMENTS 4,253,743 3/1981 Matsumura .
4,692,003 9/1987 Adachi et al. .

FOREIGN PATENT DOCUMENTS 0177005 9/1985 European Pat. Off. .
0189350 1/1986 European Pat. Off. .
3010576 3/1980 Fed. Rep. of Germany .

Primary Examiner—Paul M. Dzierzynski
Attorney, Agent, or Firm—Price, Gess & Ubell

[57] ABSTRACT

An apparatus for measuring the refractive power of eye having an optical measuring device provided with a measuring optical system and a main body for calculating the refractive power of eye based on data transmitted thereto from the optical measuring device. The optical measuring device is separate from the main body so as to be hand-movable. An examiner adjusts the position of the optical measuring device with respect to the patient's eye irrespective of the patient's posture.

16 Claims, 16 Drawing Sheets

APPARATUS FOR MEASURING REFRACTIVE POWER OF EYE

BACKGROUND OF THE INVENTION

1. Field of the invention

The present invention generally relates to a refractometer of an eye and, more particularly, to an apparatus for measuring the refractive power of an eye.

2. Description of the Related Art

Various refractometers for measuring the refractive power of an eye are known. The refractometer observes a spot pattern formed on the eyeground, namely, the retina of the eye to be examined (hereinafter referred to as eye) through an optical system so as to measure the refractive power of the eye. Before the refractive power of an eye is measured, it is necessary to adjust the position of the measuring optical system of the refractometer with respect to the eye to a measurable state, namely, the state in which the axis of the eye aligns with that of the measuring optical system and the optical pattern is formed on the retina of the eye in an in-focus condition. According to known refractometers, it is necessary for a patient to fix his eye on the visual target for several to several tens of seconds before the refractometer is capable of measuring the refractive power of eye. To this end, the patient has his forehead, chin or cheek fixed to a head fixing member. The known refractometer comprises, as shown in FIG. 28, a head fixing member 62 mounted on one end portion of a base 61, a main body 63 which is moved on the base 61 by a moving mechanism included therein, an optical measuring device 64 mounted on the main body 63, and a joy stick 65. In this construction, the joy stick 65 is operated to move the main body 63 in the lengthwise, widthwise, and vertical directions thereof so that the optical measuring device 64 is adjusted to precisely confront the eye fixed to the head fixing member 62. Thus, the known refractometer or automatic refractometer forces the patient to take an uncomfortable posture for a predetermined period of time. Thus, the patient is required to have concentration while his eye is being measured. In addition, even an adult must have patience during this period of time. Such being the case, it is very difficult to examine infants' eyes.

In the known refractometer, the refractive power of eye is measured under a condition where when the an optical pattern is correctly formed on the retina. Optical elements such as a slit and a lens are required to be movably mounted on the light projecting optical system which projects a light of the optical pattern or on the light receiving optical system which receives the light of the optical pattern reflected from the retina. This construction prevents a compact light measuring optical system and a device containing the light measuring optical system from being manufactured. Since the apparatus for measuring the refractive power of an eye has the construction as described above, the apparatus is fixed to a table. When the refractive power of an eye of a patient who is so serious that he cannot rise on the bed is measured, a particular device is required to be prepared. As such, the known apparatus has various disadvantages to be overcome.

SUMMARY OF THE INVENTION

Accordingly, it is an essential object of the present invention to provide an eye refractive power measuring apparatus which does not force a patient to take a fixed posture or make the patient feel uncomfortable and measures the refractive power of the patient's eye at a high speed.

It is another object of the present invention to provide a light source device suitable for serving as means for illuminating the eye to be examined and detecting the alignment between the optical axes of the eye and the illuminating system as well as optical axes alignment detecting system of the optical measuring device of the apparatus for measuring the refractive power of eye.

It is still another object of the present invention to provide a device for detecting the position of the optical measuring device with respect to the optical axis of an eye to be examined.

It is still another object of the present invention to provide a device having a simple construction in detecting the axis alignment between the optical axes of the eye and the illuminating system as well as the axis alignment detecting optical system.

It is a further object of the present invention to provide an apparatus for measuring the refractive power of an eye in which when the optical axis of the optical measuring device has aligned with the optical axis of an eye, the measuring optical system is actuated, whereby the data of a measurement can be obtained.

It is a still further object of the present invention to provide a device for correcting an error which may occur during a measurement due to the non-alignment between the optical axis of an optical measuring device and the optical axis of an eye.

In accomplishing these and other objects, an apparatus for measuring the refractive power of an eye in accordance with the present invention is constructed as described hereinbelow.

According to one preferred embodiment of the present invention, in an apparatus for measuring the refractive power of an eye having an optical measuring device provided with a measuring optical system for measuring the refractive power of eye and a main body for calculating the refractive power of an eye based on data transmitted thereto from said optical measuring device, wherein said optical measuring device is separated from said main body so as to be hand-movable with respect to said main body.

More specifically, the measuring optical system comprises a measuring light projecting optical system for projecting a measuring light so as to project an optical pattern on the retina of the eye; a measuring light receiving optical system in which a light reflected from the pattern projected on the retina of the eye is received by a light receiving sensor; a visual target optical system for allowing the eye to watch a visual target disposed at a far point with respect to the eye; an optical system including an illuminating optical system and an optical axes-aligned state detecting optical system which comprises an illuminating light source for illuminating the eye so that an illuminated pattern image reflected from the cornea of the eye is used as an optical axes-aligned state detecting light, the optical axes-aligned state detecting optical system allowing said light receiving sensor to receive a light reflected from the eye; and a monitor means provided at least in one of said optical measuring device and said main body so as to display the eye based on an image signal transmitted thereto from said light receiving sensor and to desplay an optical axes-aligned state detecting reticle pattern on the screen thereof. Said main body comprises, an image processing device for detecting coordinates of the illuminated pattern image and the projected pattern image with respect to an optical axis of said measuring light receiving optical system and luminances of the illuminated and projected pattern images based on image signals transmitted thereto from said light receiving sensor; optical axes-aligned state detecting means for detecting the axes-aligned state of said measuring optical system with respect to the eye based on the coordinate data of the illuminated pattern image transmitted thereto from said image processing device; in-focus state detecting a means for detecting focused state of said measuring optical system with respect to the eye based on luminance data of the illuminated pattern image transmitted thereto from said image processing device; measurement starting means for allowing said measuring light projecting optical system to project a measuring light based on focusing and axes-aligning information transmitted thereto from said optical axes-aligned state detecting means and said in-focus state detecting means; and calculating means for calculating the refractive power of eye based on the coordinate data of the illuminated pattern image transmitted thereto from said image processing device.

With the apparatus for measuring the refractive power of eye as described above, the optical measuring device serving as a means for adjusting the distance or position therefrom to the eye is separated from the main body so as to be hand-movable. Accordingly, an examiner can easily adjust the position of the optical measuring device according to the position of the patient's eye irrespective of the posture of the patient.

The examiner operates the optical measuring device so as to approach a measurable position, i.e., the examiner can adjust the distance or position therefrom to the eye while the examiner is watching the monitor screen. It is preferable to mount the monitor screen, made of a liquid crystal display which is light and compact, on the optical measuring device rather than on the main body if the examiner does not have difficulty in performing his operation. According to this construction, the examiner can perform the measuring operation watching the same portion, namely, the optical measuring device. Thus, the operability of the apparatus is favorable. The monitor screens may be mounted on both the optical measuring device and the main body. According to this construction, an image is displayed on the monitor screen mounted on the optical measuring device when the optical axes-aligned and in-focus state are being adjusted and measured values are displayed on the monitor screen mounted on the main body after the refractive power of eye is measured.

The illuminating light source for illuminating the eye serves as a light source for adjusting optical axes-aligned and in-focus states and the light receiving sensor receives both the measuring light and the axes-aligned state detecting light. Therefore, the measuring optical system is compact.

When axes-aligned and in-focus states are obtained, the axes-aligned state detecting means and the in-focus state detecting means instantly measure and calculate the refractive power of eye.

It is preferable that the light source of the illuminating optical system and the axes-aligned state detecting optical system comprises a plurality of spot light sources disposed circumferentially of the optical axis of the measuring light projecting optical system and symmetrically with each other with respect thereto.

According to the above-described construction, the illuminating light source serves as a light for detecting an axes-aligned state. These illuminating light sources are arranged so as to confront each other symmetrically with respect to the axis of the measuring light. Accordingly, the optical axis of a projected measuring light coincides with the center of the illuminating light sources. According to this construction, if the respective illuminating light sources are equally spaced from the optical axis of the eye, the monitor means displays that the center of the eye coincides with the center of a circle formed by connecting the illuminated pattern images reflected from the cornea. In other words, if the optical axis of the eye is not coincident with the center of the illuminated pattern images, the monitor means displays that the pattern images are shifted from the eye to be measured. Thus, the following can be detected: the direction in which the optical axis of the light illuminated by the light source is in non-alignment with that of the eye; and the amount of the non-alignment therebetween. Further, according to the pattern images of the illuminating light sources, it is detected by various known methods whether or not an in-focus condition has been obtained. As described above, the illuminating light source for illuminating the eye serves as the light for detecting axes-aligned and in-focus states. Accordingly, the measuring optical system is compact.

It is preferable that a plurality of said spot light sources are supported by a disk member mounted on the housing of said optical measuring device so as to be rotatable about said optical axis and a weight for maintaining the posture of said disk member is fixed to said disk member at a predetermined position thereof so that predetermined spot light sources continually take predetermined positions; said main body comprises; means for selectively turning on said predetermined light sources; and means for detecting the posture of said optical measuring device with respect to the eye based on the coordinates of the illuminated spot images corresponding to said predetermined light sources detected by said image processing device.

According to the above-described construction, the posture of the optical measuring device relative to the eye is detected. The above-described construction is very effective for measuring the refractive power of an eye for the optical measuring device which is hand-movable with respect to the eye.

It is preferable that the image processing device comprises a means for detecting the high frequency component of the illuminated pattern image and that the in-focus state detecting means includes means for comparing the high frequency component of the illuminated pattern image with a reference value and deciding that an in-focus state is obtained when the high frequency component is greater than the reference value.

According to this construction, a deciding means can be constructed with software by using a microcomputer. Thus, the in-focus state can be detected with a high accuracy by a simple construction.

According to another preferred embodiment of the present invention, there is provided an apparatus for measuring the refractive power of an eye having an optical measuring device provided with a measuring optical system for measuring the refractive power of eye and a main body for calculating the refractive power of the eye based on data transmitted thereto from said optical measuring device.

The measuring optical system comprises a measuring light projecting optical system for projecting a measuring light so as to project a pattern on the retina of the eye; a measuring light receiving optical system in which a light reflected from the pattern projected on the retina of the eye is received by a light receiving sensor; a visual target optical system for allowing the eye to watch a visual target disposed at a far point with respect to the eye; and an optical system including an illuminating optical system and an optical axes-aligned state detecting optical system which comprises an illuminating light source for illuminating the eye so that a illuminated pattern image reflected from the cornea of the eye is used as an optical axes-aligned state detecting light, the optical axes-aligned state detecting optical system allowing said light receiving sensor to receive a light reflected from the eye.

A monitor means is provided at least in one of said optical measuring device and said main body so as to display the eye based on an image signal transmitted thereto from said light receiving sensor and to display an optical axes-aligned state detecting reticle pattern on the screen thereof.

The main body comprises means for detecting in-focus and optical axes-aligned states of the measuring optical system with respect to the eye based on the image signal transmitted thereto from said light receiving sensor; measurement starting means for allowing the measuring light projecting system to project a measuring light based on the focusing and axes-aligning information transmitted thereto from said means for detecting focusing and optical axes-aligned states; and a calculating means for calculating the refractive power of eye based on the information of the projected pattern image transmitted thereto from said light receiving sensor.

According to still another preferred embodiment in accordance with the present invention, there is provided an apparatus for measuring the refractive power of eye having an optical measuring device provided with a measuring optical system for measuring the refractive power of eye and a main body for calculating the refractive power of eye based on data transmitted thereto from said optical measuring device.

The measuring optical system comprises a measuring light projecting optical system for projecting a measuring light so as to project a pattern on the retina of the eye; a measuring light receiving optical system in which a light reflected from the pattern projected on the retina of the eye is received by a light receiving sensor; a visual target optical system for allowing the eye to watch a visual target disposed at a far point with respect to the eye; an illuminating optical system for illuminating the eye so that a light reflected from the eye is received by said light receiving sensor, and an optical axis-alinged state detecting system which has a light source and allows said light receiving sensor to receive the light reflected from the eye.

Monitor means is provided at least in one of said optical measuring device and said main body so as to display the eye based on an image signal transmitted thereto from said light receiving sensor and to desplay an optical axes-alinged state detecting reticle pattern on the screen thereof.

The main body comprises means for detecting in-focus and optical axes-aligned states of the measuring optical system with respect to the eye based on the image signal transmitted thereto from said light receiving sensor; measurement starting means for allowing the measuring light projecting system to project a measuring light based on the focusing and axes-aligning information transmitted thereto from said means for detecting focusing and optical axes-aligned states; and a calculating means for calculating the refractive power of eye based on the information of the projected patter image transmitted thereto from said light receiving sensor.

According to a further preferred embodiment in accordance with the present invention, there is provided an apparatus for measuring the refractive power of an eye having an optical measuring device provided with a measuring optical system for measuring the refractive power of an eye and a main body for calculating the refractive power of an eye based on data transmitted thereto from said optical measuring device.

The measuring optical system comprises a measuring light projecting optical system for projecting a measuring light so as to project an optical pattern on the retina of the eye; a measuring light receiving optical system in which a light reflected from the pattern projected on the retina of the eye is received by a light receiving sensor; an optical system including an illuminating optical system and an optical axes-aligned state detecting optical system which comprises an illuminating light source for illuminating the eye so that an illuminated pattern image reflected from the cornea of the eye is used as an optical axes-aligned state detecting light, and the optical axes-aligned state detecting optical system allowing said light receiving sensor to receive a light reflected from the eye.

The main body comprises an image processing device for detecting coordinates of the illuminated pattern image and the projected pattern image with respect to an optical axis of said measuring light receiving optical system and luminances of the illuminated and projected pattern images based on image signals transmitted thereto from said light receiving sensor, optical axes-aligned state detecting means for detecting the axes-aligned state of said measuring optical system with respect to the eye based on the coordinate data of the illuminated pattern image transmitted thereto from said image processing device; in-focus state detecting means for detecting focused state of said measuring optical system with respect to the eye based on luminance data of the illuminated pattern image transmitted thereto from said image processing device; measurement starting means for allowing said measuring light projecting optical system to project a measuring light based on focusing and axes-aligning information transmitted thereto from said optical axes-aligned state detecting means and said in-focus state detecting means, and calculating means for calculating the refractive power of the eye based on the coordinate data of the illuminated pattern image transmitted thereto from said image processing device.

According to a still further preferred embodiment in accordance with the present invention, there is provided an apparatus for measuring the refractive power of an eye having an optical measuring device provided with a measuring optical system for measuring the refractive power of an eye and a main body for calculating the refractive power of the eye based on data transmitted thereto from said optical measuring device.

The measuring optical system comprises a measuring light projecting optical system for projecting a measuring light so as to project a pattern on the retina of the eye; a measuring light receiving optical system in which a light reflected from the pattern projected on the retina of the eye is received by a light receiving sensor; an illuminating optical system for illuminating the eye so that a light reflected from the eye is received by said light receiving sensor 29; and an optical axis-alinged state detecting system which has a light source and allows said light receiving sensor to receive the light reflected from the eye.

The main body comprises means for detecting in-focus and optical axes-aligned states of the measuring optical system with respect to the eye based on the image signal transmitted thereto from said light receiving sensor; measurement starting means for allowing the measuring light projecting system to project a measuring light based on the focusing and axes-aligning information transmitted thereto from said means for detecting focusing and optical axes-aligned states, and a calculating means for calculating the refractive power of the eye based on the information of the projected pattern image transmitted thereto from said light receiving sensor.

According to a still another preferred embodiment in accordance with the present invention, there is provided an apparatus for measuring the refractive power of an eye having an optical measuring device provided with a measuring optical system for measuring the refractive power of the eye and a main body for calculating the refractive power of the eye based on data transmitted thereto from said optical measuring device.

The measuring optical system comprises an optical system including an illuminating optical system and an optical axes-aligned state detecting optical system which comprises an illuminating light source for illuminating the eye so that an illuminated pattern image reflected from the cornea of the eye is used as an optical axes-aligned state detecting light, the optical axes-aligned state detecting optical system allowing said light receiving sensor to receive a light reflected from the eye, said illuminating light source comprising a plurality of spot patterns sources disposed circumferentially of the optical axis of a measuring light projecting optical system and symmetrically with each other with respect thereto.

The main body includes means for detecting in-focus and optical axes-aligned states of said measuring optical system based on an image signal transmitted thereto from said light receiving sensor.

The present invention provides the apparatus for measuring the refractive power of eye including a means for correcting an error due to the non-alignment between the optical axes of the measuring optical system and the eye. That is, the apparatus for measuring the refractive power of an eye comprises an optical measuring device provided with a measuring optical system for measuring the refractive power of eye and a main body for calculating the refractive power of eye based on data transmitted thereto from said optical measuring device.

The measuring optical system comprises a measuring light projecting optical system for projecting a measuring light so as to project a pattern on the retina of the eye; and a measuring light receiving optical system for allowing a light receiving sensor to receive a light reflected from the pattern projected on the retina of the eye.

The projective pattern of the measuring light including two spot lights spaced from each other by 90° with respect to and in the circumference of the optical axis of said measuring light projecting optical system.

The measuring light receiving optical system including on the optical axis thereof an eyepiece which condenses lights reflected from spot images formed on the retina of the eye, a diaphragm which allows the passages of the light beams which have been reflected from the retina and passed through said eyepiece, an image forming lens which allows the passages of the light beams which have passed through said diaphragm, and said light receiving sensor which receives the lights of the spot images formed by the image forming lens.

The diaphragm is substantially conjugate to the cornea of the eye with respect to the eyepiece and having an aperture small enough to select a light beam from light beams reflected from spot images formed on the retina so as to allow the passage of said light beam which passes the point at which the cornea and the optical axis of said measuring light receiving optical system cross each other.

According to the above-described construction, since sufficiently small spot images can be formed on the light receiving sensor, the accurate position of the spot images can be determined on the light receiving sensor. Thus, a measured value including no errors or very few errors is obtained by performing a calculation according to predetermined equations based on the data of the spot images outputted from the light receiving sensor to the microcomputer.

The present invention further provides the apparatus for measuring the refractive power of eye including a means for correcting an error due to the non-alignment of optical axes.

That is, the apparatus for measuring the refractive power of an eye comprises an optical measuring device provided with measuring optical system for measuring the refractive power of an eye and a main body for calculating the refractive power of an eye based on data transmitted thereto from said optical measuring device.

The measuring optical system comprises a measuring light projecting optical system for projecting a measuring light so as to project a pattern on the retina of the eye and a measuring light receiving optical system for allowing a light receiving sensor to receive a light reflected from the pattern projected on the retina of the eye.

The projective pattern of the measuring light including four spots spaced from each other by 90° with respect to and in the circumference of the optical axis of said measuring light projecting optical system.

The measuring light receiving optical system including on the optical axis $a_1$ thereof an eyepiece which condenses lights reflected from spot images formed on the retina of the eye, an image forming lens which allows the passage of the light beams which have been reflected from the spot images formed on the retina of the eye and passed through said eyepiece, and said light receiving sensor which receives the lights of the spot images formed by the image forming lens.

The main body comprises first calculating means for calculating, based on position data of each pair of spot images detected by the light receiving sensor, the height ($h_0$) of a pair of spot images corresponding to the height (h) of points (Q) and (Q') of the spots projected on the retina of the eye by said measuring light projecting optical system in which two spot images of each pair received by said light receiving sensor are symmetrical with respect to the optical axis of said measuring light receiving optical system and the height (h) of said spot images (Q) and (Q') correspond to the distance from the optical axis $a_E$ of the eye, and second calculating means for calculating the refractive power of eye based on said height ($h_0$).

According to the above-described construction, since the height ($h_0$) of the spot images formed on the light receiving sensor is obtained by the data of the positions thereof by projecting two measuring lights from the measuring light projecting optical system. Therefore, the non-alignment between both optical axes does not cause an error in measuring the height ($h_0$) of the spot images formed on the light receiving sensor by using a predetermined equation based on the data of the positions of the spot images of each of the pair.

More specifically, the first calculating means calculates the first height ($h_0$)' of one of the two spot images and the second height ($h_0$") of the other thereof per each pair with respect to the optical axis of the measuring light receiving optical system detected by the light receiving sensor, and according to an equation of $$h_0 = \frac{h0' - h0''}{2},$$

calculates the height ($h_0$) of the two spot images corresponding to the height (h) of the points of the lights on the retina of the eye projected by the measuring light projecting optical system in which the height of the points are the distance from the optical axis of the measuring light receiving optical system.

According to the above-described construction, it is preferable to provide the measuring light receiving optical system with a diaphragm between the eyepiece and the image forming lens.

Preferably, the diaphragm is disposed in a position conjugate to the cornea with respect to the eyepiece and has an aperture whose diameter is great enough to allow the passage therethrough of a light beam having an amount of light necessary for the light receiving sensor to detect a spot image formed on the light receiving sensor.

This construction comprises the combination of the first and second constructions for correcting the non-alignment of optical axes. According to the first construction, the heights of the spot images formed on the light receiving sensor are calculated by using lights selected by the diaphragm. According to the second construction, the refractive power of the eye is calculated based on the calculation performed by the first construction. That is, the calculations for correcting the error caused by the non-alignment of optical axes are performed twice. Therefore, the heights of the spot images formed on the light receiving sensor are very accurate, hence very reliable.

The present invention also provides an apparatus for measuring the refractive power of an eye which performs a processing for an error when the error amount due to the non-alignment of the optical axes is great.

The apparatus comprises an optical measuring device provided with a measuring optical system for measuring the refractive power of an eye and a main body for calculating the refractive power of the eye based on the data transmitted thereto from the optical measuring device.

The measuring optical system comprises a measuring light projecting optical system for projecting a measuring light so as to project a pattern on the retina of the eye and a measuring light receiving optical system in which a light reflected from the pattern projected on the retina of the eye is received by a light receiving sensor.

The projected pattern of the measuring light includes four spots spaced from each other by 90° with respect to and in the circumference of the optical axis of the measuring light projecting optical system.

The main body includes a deciding means for deciding the error amount between the optical axis of the measuring light optical system and the optical axis of the eye based on the positions of the images of four patterns relative to the optical axis of the measuring light receiving optical system; a comparing means for comparing the error amount with a reference value; and a means for performing an error processing by deciding that an error has occurred when the error amount is greater than the reference value.

According to the above construction, since two pairs of spot light sources are projected by the measuring light projecting optical system, the positions of the spot images relative to the axis of the eye, namely, the error amount caused by the non-alignment between the optical axes of the measuring light optical system and the eye can be correctly detected by performing relatively easy calculations. If it is decided by the deciding means and the error processing means that the error amount between both optical axes is great, the examiner can recognize that the measurement is erroneous. Therefore, the examiner can correctly measure the refractive power of eye.

BRIEF DESCRIPTION OF THE DRAWINGS

These and other objects and features of the present invention will become apparent from the following description taken in conjunction with the preferred embodiments thereof with reference to the accompanying drawings, in which:

FIG. 3 through FIG. 8 are views showing the optical systems composing the measuring optical system in which;

FIG. 3 shows a measuring light projecting optical system;

FIG. 4 shows a measuring light receiving optical system;

FIG. 5 shows an illuminating optical system; and

FIGS. 6 and 7 show a monitoring camera optical system composing an optical axes-aligned state detecting optical system and a monitoring reticle optical system composing the axes-aligned state detecting optical system;

FIG. 8 shows a visual target optical system;

FIGS. 9 and 10 are explanatory views explaining axes-aligning conditions of lights reflected from a cornea depending on the position of an illuminating light source; in which;

FIG. 9 shows the state in which optical axes are not aligned with each other;

FIG. 10 shows the state in which optical axes align with each other;

DETAILED DESCRIPTION OF THE INVENTION

Figure 1:
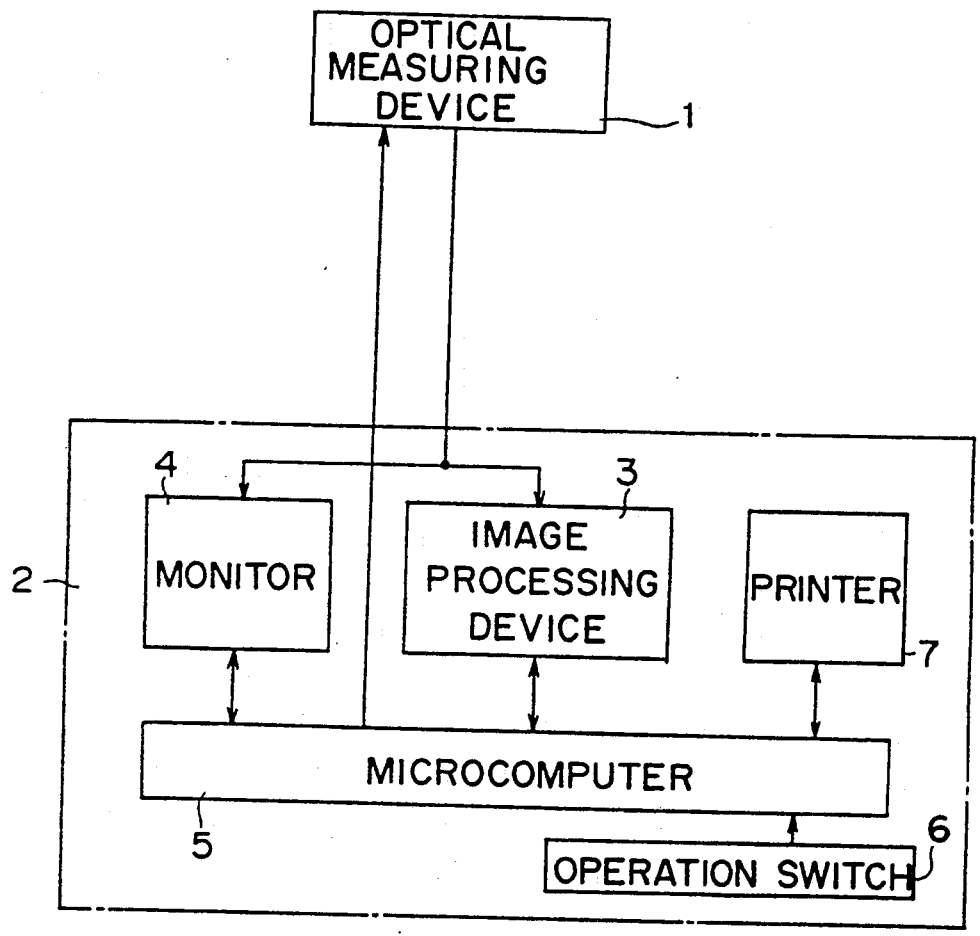
FIG. 1 is a block diagram showing the construction of an apparatus for measuring the refractive power of eye according to one embodiment of the present invention.

Before the description of the present invention proceeds, it is to be noted that like parts are designated by like reference numerals throughout the accompanying drawings.

Figure 20:
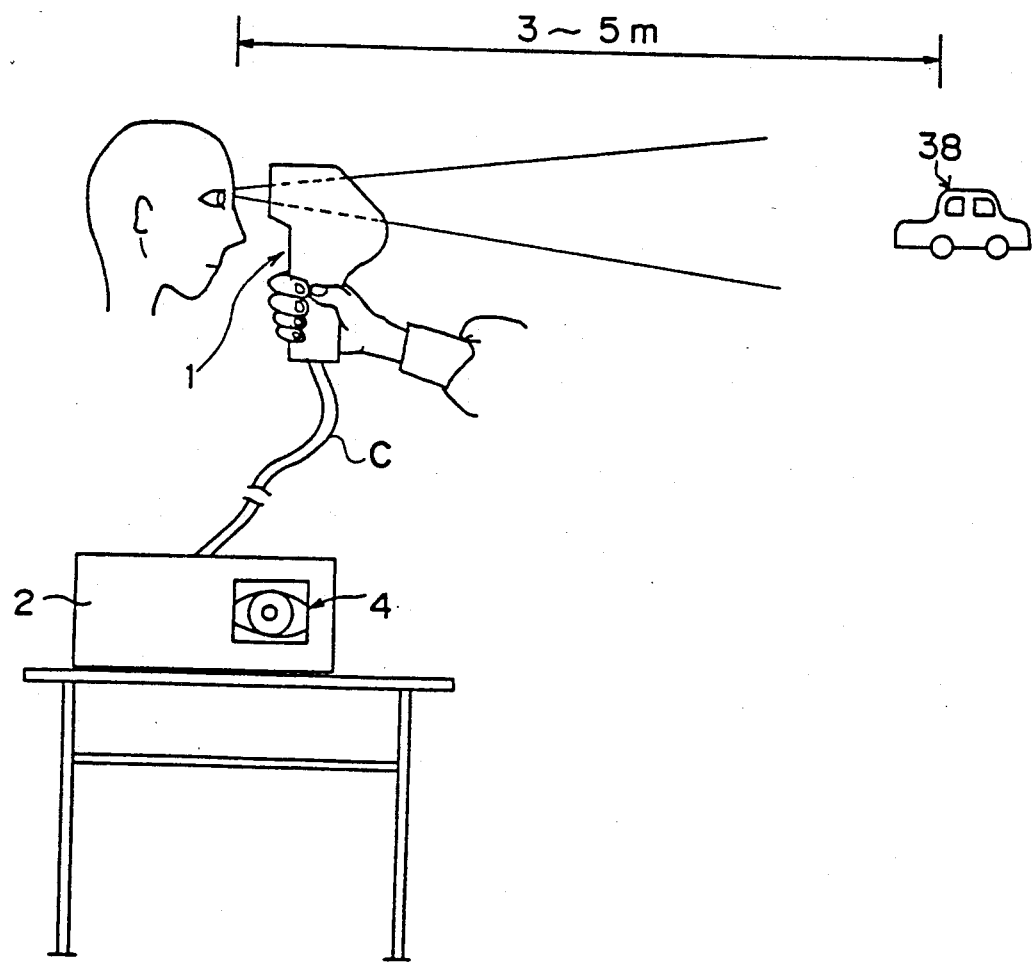
FIG. 20 is a view showing the state in which the refractive power of an eye is measured.

Referring now to the drawings, there is shown in FIG. 1, an apparatus for measuring the refractive power of eye in accordance with the present invention. As shown in FIG. 1, the apparatus for measuring the refractive power of eye comprises an optical measuring device 1 and a main body 2. The optical measuring device 1 contains a measuring optical system which is so small and light as to be movable in one hand. The main body 2 comprises an image recognizing device or an image processing device 3 for detecting optical axes-aligned and in-focus conditions based on an image signal applied thereto from the optical measuring device 1 and a monitor 4 for displaying the image on its screen based on the image signal from the oprical measuring device 1. The main body 2 further comprises a microcomputer 5 which exchanges data with the image recognizing device 3 and the monitor 4, thus outputting a control signal to the optical measuring device 1 and calculating the refractive power of eye based on the data from the image signal inputted to the image processing device 3. When the image processing device 3 detects that the optical axis of the measuring optical system has aligned with that of the eye to be examined (hereinafter referred to as eye) and an image has been formed on the retina of the eye, the microcomputer 5 applies a measurement starting signal to the measuring optical system. Thereafter, the microcomputer 5 calculates the refractive power of the eye based on the image information applied thereto from the image processing device 3. The microcomputer 5 is connected with an operation switch 6. A printer 7 outputs the data calculated by the microcomputer 5 and outputted from the microcomputer 5 thereto. The optical measuring device 1 and the main body 2 are connected to each other by a cable C as shown in FIG. 20 or wireless telegraphy. The optical measuring device 1 is movable so as to adjust the position thereof with respect to eye whereas the main body 2 is fixed to a table or the like. Accordingly, an examiner can easily adjust the distance therebetween by moving the optical measuring device 1 in one hand.

Figure 2:
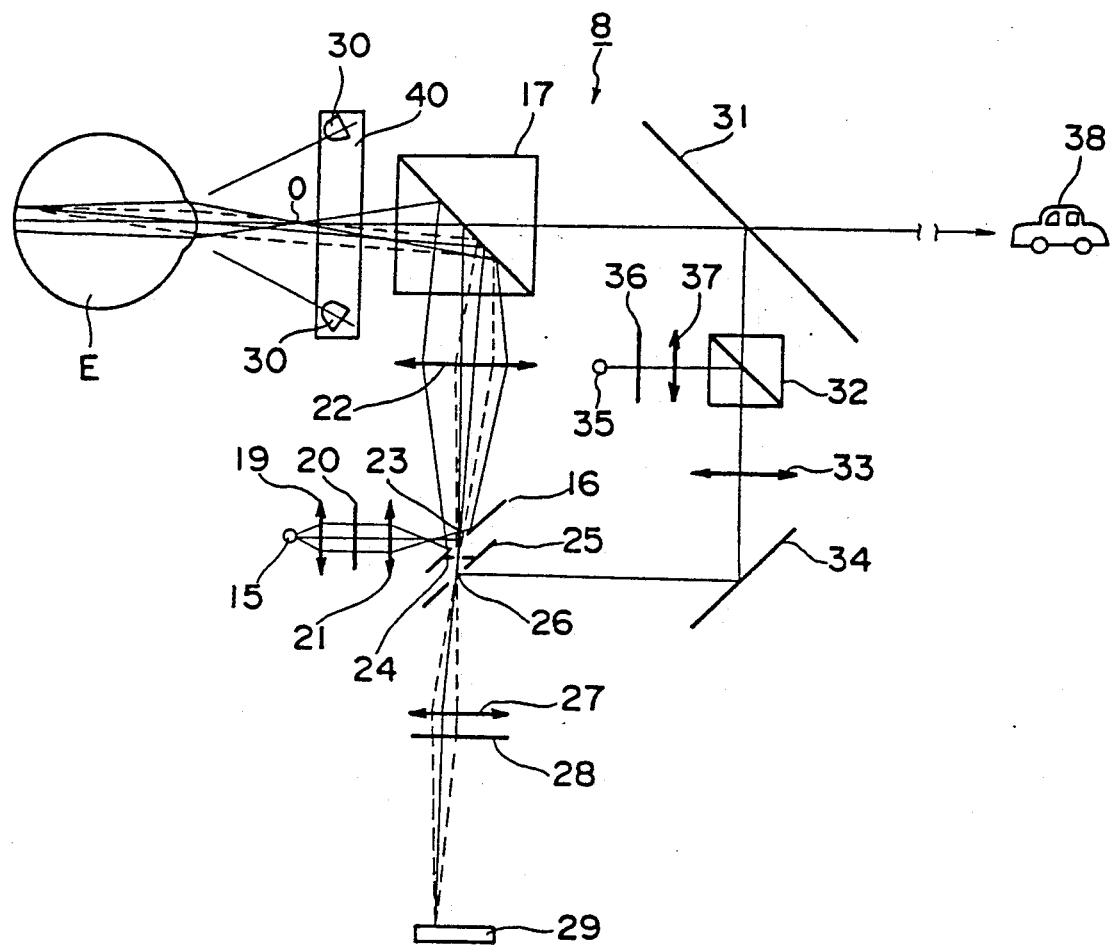
FIG. 2 is a view showing a measuring optical system contained in the optical measuring device shown in FIG. 1.

FIG. 2 shows a measuring optical system 8 included in the optical measuring device 1. FIG. 3 through 8 show the optical systems composing the measuring optical system 8, namely, a measuring light projecting optical system 9 (FIG. 3), a measuring light receiving optical system 10 (FIG. 4), a visual target optical system 11 (FIG. 8), an optical axes-aligned state detecting optical system comprising a monitoring camera optical system 12 (FIG. 6) and a monitoring reticle optical system 13 (FIG. 7) and a monitoring illuminating optical system 14 (FIG. 5).

Figure 3:
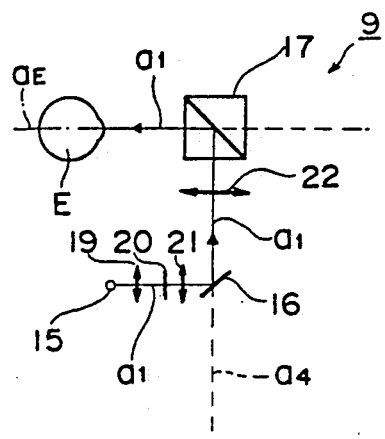

Referring to FIG. 3 showing the measuring light projecting optical system 9, infrared measuring rays emitted by a light source 15 are reflected upward at an angle of 90° by a first reflecting mirror 16 because the first reflecting mirror 16 forms 45° with the optical axis $a_1$. A first prism 17 composed by cementing the hypotenuses of rectangular prisms with each other is disposed on the optical axis $a_1$ so that the cemented face may form 90° with first reflecting mirror 16, whereby the infrared measuring rays are reflected by the first prism 17 at an angle of 90°. The first prism 17 which is a half prism reflects the infrared rays at some percentage and transmits the remaining infrared rays therethrough while it transmits almost all visible rays therethrough. Therefore, it is required for the eye (E) to be positioned on the optical axis $a_1$ so that the infrared measuring rays reach the retina. A collimator lens 19, a light projecting pattern mask 20, and a light projecting relay lens 21 are disposed in this order on the optical axis $a_1$ between the light source 15 and the first reflecting mirror 16. An eyepiece 22 is disposed on the optical axis $a_1$ between the first reflecting mirror 16 and the first prism 17. The measuring rays emitted by the light source 15 travels from the collimator lens 19, the light projecting pattern mask 20, the light projecting relay lens 21, the first reflecting mirror 16, the eyepiece 22, and to the first prism 17. Thereafter, the rays are incident on the eye (E) in the order of the pupil, the cornea surface, and the crystalline lens, thus projecting the pattern of the light projecting pattern mask 20 on the retina.

Figure 4:
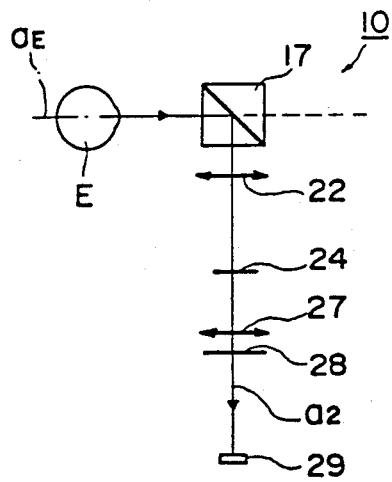
Figure 5:
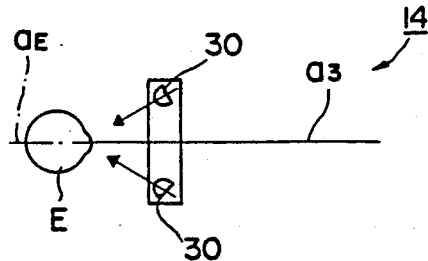

Referring to FIG. 4, the light receiving optical system 10 for receiving the measuring light is described hereinbelow. The measuring light reflected from the retina on which the projected pattern has been formed travels back along an optical axis $a_2$ of the light receiving optical system 10. As shown in FIG. 2, when the measuring light reaches the first reflecting mirror 16, it passes through a first opening 23 formed in approximately the center of the first reflecting mirror 16. As also shown in FIG. 2, a diaphragm 24 is formed directly below the first opening 23 and there is provided directly below the diaphragm 24 a second opening 26 formed in approximately the center of a second reflecting mirror 25 which is described later. Therefore, the measuring light which has passed through the first opening 23 rectilinearly travels through the diaphragm 24 and the second opening 26. Thus, the measuring light which has returned to the first reflecting mirror 16 along the optical axis $a_1$ goes downward rectilinearly along the optical axis $a_2$, thus reaching a light receiving sensor through an image forming lens 27 and a filter 28. The diaphragm 24 is disposed to be substantially conjugate to the eyepiece 22 with respect to the cornea. Owing to this arrangement, a measured error due to a slight non-alignment between the optical axis of the eye and that of the measuring optical system 8 can be automatically compensated. Therefore, even through the hand-movable optical measuring device 1 is shaken, the measured error which is caused by the non-alignment between the optical axis of the eye and that of the measuring optical system 8 can be minimized. The description of the principle of this mechanism will be made later.

Figure 11:
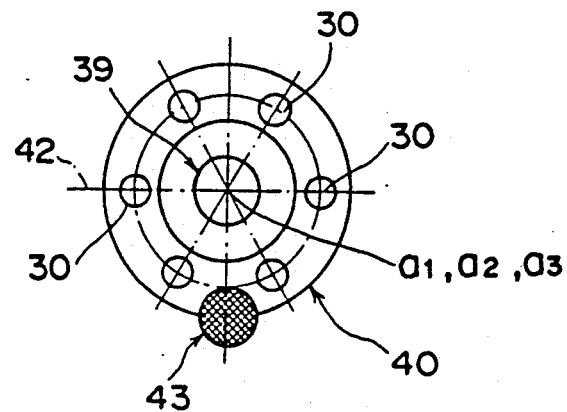
FIG. 11 is a view showing the state in which the illuminating light source and a weight are mounted on a disk member.

Referring to FIG. 5, the monitoring illuminating optical system 14 comprising six infrared light sources 30 is described hereinbelow. As shown in FIG. 11, the six infrared light sources 30 are concentrically spaced from each other at an interval of 60° in the periphery of the optical axis $a_3$ of the monitoring illuminating optical system 14. The optical axis $a_3$ is in alignment with the optical axis $a_1$ of the measuring light. Since the light is emitted by the infrared light sources 30, the eye does not feel the light, and as such, is not dazzled by the light.

Figure 6:
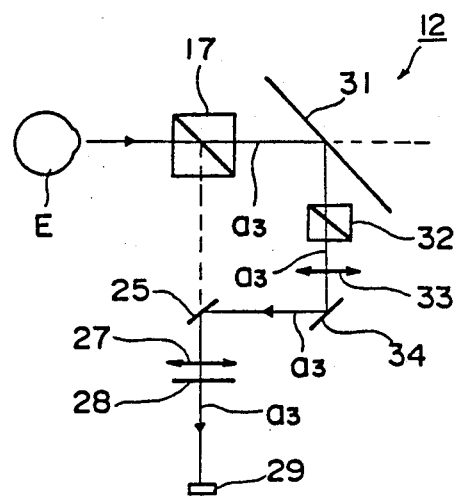
Figure 9:
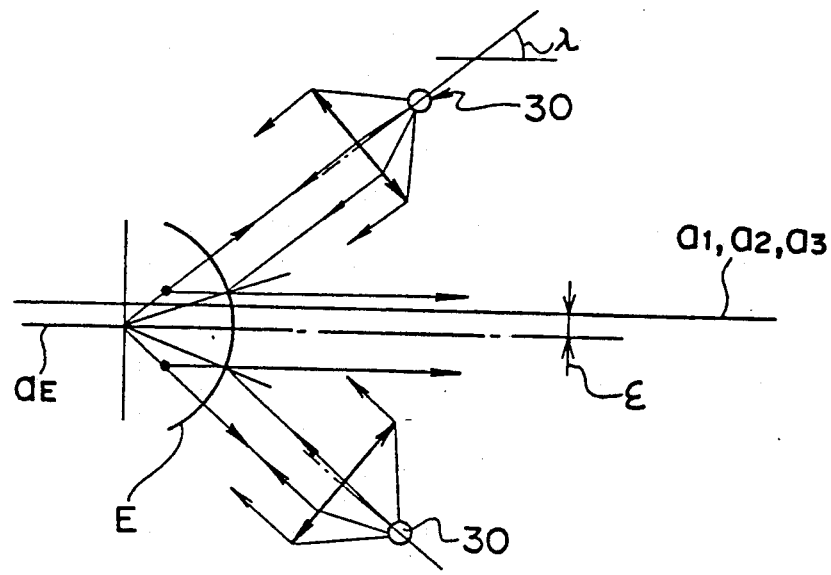
Figure 10:
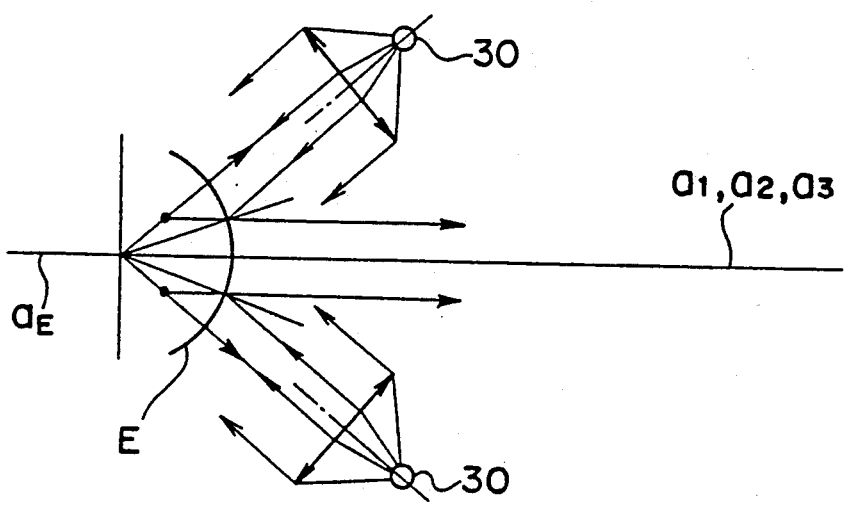

It is to be noted that the light emitted by the monitoring illuminating optical system 14 is reflected from the cornea and that the optical measuring device 1 uses the light reflected by the cornea as a light to detect an axis alignment detecting light. To this end, the monitoring camera optical system 12 is constructed as shown in FIG. 6, the construction of which is described later. As shown in FIGS. 9 and 10, when parallel beams which form λ with the optical axis $a_3$ of the illuminating optical system is projected toward the eye (E) in the condition in which the optical axis $a_E$ of the eye (E) does not align with the optical axis $a_3$ of the monitoring illuminating optical system 14, the center (the optical axis ($a_E$) of the eye (E)) of a circle formed by connecting six images formed by the six beams (optical axes alignment detecting light) which has been reflected from the cornea does not align with the optical axis $a_3$ of the monitoring illuminating optical axis. Theoretically, an optical axes-aligned state can be obtained by measuring the error amount ($\epsilon$) between both optical axes and marking the error amount zero. The signal level of the bright spots of the light source 30 reflected from the cornea is more than three times as strong as the levels of the other image signals. Utilizing this characteristic, an in-focus state can be detected. That is, when the in-focus state is obtained, the area of the bright spots of the light on the cornea is smallest and the contrast thereof becomes highest. This is detected by the image processing device 3. The optical axes-aligning and focusing operations can be simultaneously accomplished at a high speed because the examiner pays his attention to one object, namely, the reflected bright spots on the cornea. The optical axes of the measuring and monitoring optical systems can be aligned with the optical axis $a_E$ of the eye (E) by thus obtaining the optical axes-aligned condition in the monitoring illuminating optical system 14, whereby the measuring operation can be easily carried out. Further, the distance between the optical measuring device 1 and the eye (E), and more particularly, the distance between the eyepiece 22 of the measuring light projecting optical system 9 and the cornea of the eye (E) can be set to be constant suitable for examining the refractive power of the eye (E) by obtaining the in-focus state. Referring to FIG. 6, assuming that the illuminating direction is the front, there is provided rearward of a first prism 17, which partly transmits infrared rays therethrough, disposed on the optical axis $a_3$ of the monitoring illuminating optical system 14 a dichroic mirror 31 which reflects infrared ray and transmits a visible light therethrough. The dichroic mirror 31 forms 45° with the optical axis $a_3$ so that it reflects an optical axes alignment detecting light (infrared ray) at an angle of 90° downward. There is disposed on the optical axis of lights refracted at the angle of 90° downward by the dichroic mirror 31 at a second prism 32 which, contrary to the first prism 17, transmits most of infrared rays therethrough and reflects most of visible lights. The infrared rays which have been reflected by the dichroic mirror 31 pass through the second prism 32 and a monitoring lens 33 disposed below the second prism 32, thus rectilinearly traveling downward and being incident on a third reflecting mirror 34 disposed below the monitoring lens 33. The infrared rays reflected at an angle of 90° are incident on a second reflecting mirror 25. The optical axis $a_3$ intersects with the optical axis $a_2$ of the measuring light receiving optical system 10 on the plane extended from the second reflecting mirror 25. More exactly, both intersect with each other in the second opening 26. The infrared rays are reflected by the second reflecting mirror 25 downward at a right angle and travels along the optical axis $a_3$, thus reaching the light receiving sensor 29.

Figure 7:
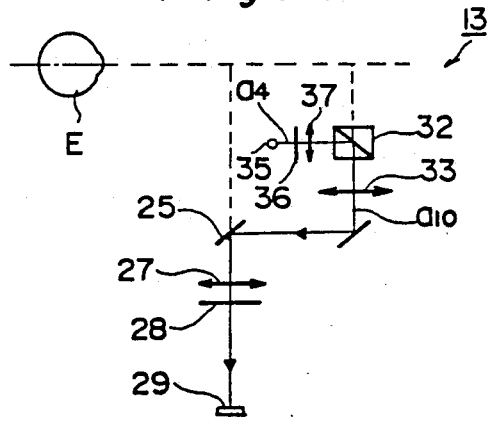

There is shown in FIG. 7 the monitoring reticle optical system 13. A light source 35, a reticle pattern mask 36, and a reticle objective lens 37 are provided in this order on one side of the second prism 32. The light source 35 emits a visible light in order to display a reticle pattern on which optical axes are aligned with each other. A light emitted by the light source 35 passes through the reticle pattern mask 36 along the optical axis $a_4$, thus serving as the reticle pattern light. Thereafter, the light passes through the reticle objective lens 37, then is refracted downward at a right angle by the second prism 32. The reticle pattern is displayed, for example, by a concentric double circle, the inner circle of which corresponds to the minimum measurable diameter of the pupil of the eye (E) and the outer circle of which is disposed at the reference position on which the spot bright images reflected from the cornea are disposed. The optical axis $a_4$ of the light refracted downward at an angle of 90° by the second prism 32 aligns with the optical axis $a_3$ of the optical axes alignment detecting light (infrared rays) emitted by the light source 30. Accordingly, the optical members of the monitoring reticle optical system 13 disposed subsequent to the second prism 32 is the same as those of the monitoring camera optical system 12. The optical path of the optical optical axes alignment detecting light subsequent to the second prism 32 aligns with the optical path of the reticle light. Accordingly, when the center of the six illuminating lights (spot image) reflected by the cornea coincide with the optical axis $a_3$ of the monitoring illuminating optical system, the center of the six illuminating lights by the cornea and the center of the reticle pattern coincide with each other. The detection of the coincidence of the centers by the light receiving sensor 29 means that the optical axes-aligned state has been obtained. The reticle pattern is necessary for displaying a reference on which the axes of the eye and the reticle optical system align with each other. Therefore, in addition to the method for obtaining the reticle pattern by means of the light source 35 and the reticle pattern mask 36 as described, a reticle pattern can also be obtained as follows: a reticle pattern is drawn on the monitor screen or a transparent glass plate which allows the passage of infrared rays is located on a position conjugate to the eye (E) with respect to the monitor relay lens 33 provided in the monitoring camera optical system 12 so that the pattern is detected by the light receiving sensor 29.

Figure 8:
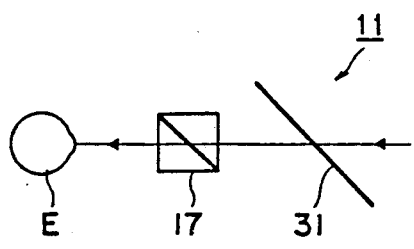

FIG. 8 shows the visual target optical system 11. As described above, the dichroic mirror 31 disposed on the optical axis $a_3$ rearward of the first prism 17 transmits a visible light therethrough. The patient can see an object 38 as shown in FIG. 20, or an optical pattern disposed rearward of the optical axis $a_3$ through the first prism 17 and the dichroic mirror 31. The optical axis $a_E$ of the eye (E) can be substantially aligned with the optical axis $a_5$ when the eye (E) is fixed on the target 38.

As described above, the light source 30 of the monitoring illuminating optical system 14 serves as the light source of the optical axes alignment detecting light and the light receiving sensor 29 is capable of detecting the axes alignment detecting light and the measuring light. Thus, the measuring optical system 8 is compact. Thus, the optical measuring device 1 can be moved by hand.

As shown in FIG. 11, the light source 30 is disposed in the periphery of an eye examining window 39. A disk member 40 rotatable about the optical axis $a_1$ ($a_2$ and $a_3$) is mounted on an unshown housing of the measuring optical device 1 so that the disk member is disposed in the periphery of the eye examining window 39. The light source 30 is secured to the disk member 40. A weight 43 is mounted on the disk member 40 so that two illuminating light sources 30 are disposed on a horizontal reference diameter 42. This construction allows the disk member 40 and the illuminating light sources 30 to maintain the same positions even though the optical measuring device 1 tilts. This construction may shake the illuminating light sources 30, which is unfavorable in measuring the eye (E). However, since the optical axes-aligning operation is performed slowly and carefully, no problem occurs in eye examinations. The microcomputer 5 provided in the main body 2 controls the illuminating light sources 30 so that a pair of illuminating light sources 30 disposed on the reference diameter are turned on when the other light sources 30 are turned off and vice versa. If the optical measuring device 1 tilts relative to the horizontal direction, the coordinates of a pair of spot images displayed on the monitor screen corresponding to a pair of the illuminating light sources disposed on the reference diameter can be obtained by the image processing device 3. Therefore, in order to know which of a pair of spot patterns is horizontal, only a pair of illuminating light sources disposed on the reference diameter is turned on and the other illuminating light sources are turned off or vice versa. This controlling operation is performed in a moment, so that the patient does not feel the monitor screen dark. Since the inclination of the optical measuring device 1 with respect to the horizontal direction is obtained, a correction is made by subtracting the inclination from a cylinder axis (AXIS) which is one of the calculated results. Thus, a correct value is displayed on the monitor screen.

Various patterns mask 20 of the measuring light projecting optical system 9 can be used. For example, a circular pattern formed around the optical axis $a_1$ and having a predetermined radius; and similarly to this circular pattern, spot patterns disposed around the circumference of the optical axis $a_1$ by a predetermined distance apart therefrom and concentrically spaced from each other at an angular interval of of, for example, 90°, 60° or 45°. In this embodiment, spot patterns are disposed concentrically spaced from each other at an angular interval of 90°.

The refraction power of eye is measured as follows by the light projecting and receiving optical systems 9 and 10 of the eye refraction power measuring apparatus constructed as described above.

Figure 12:
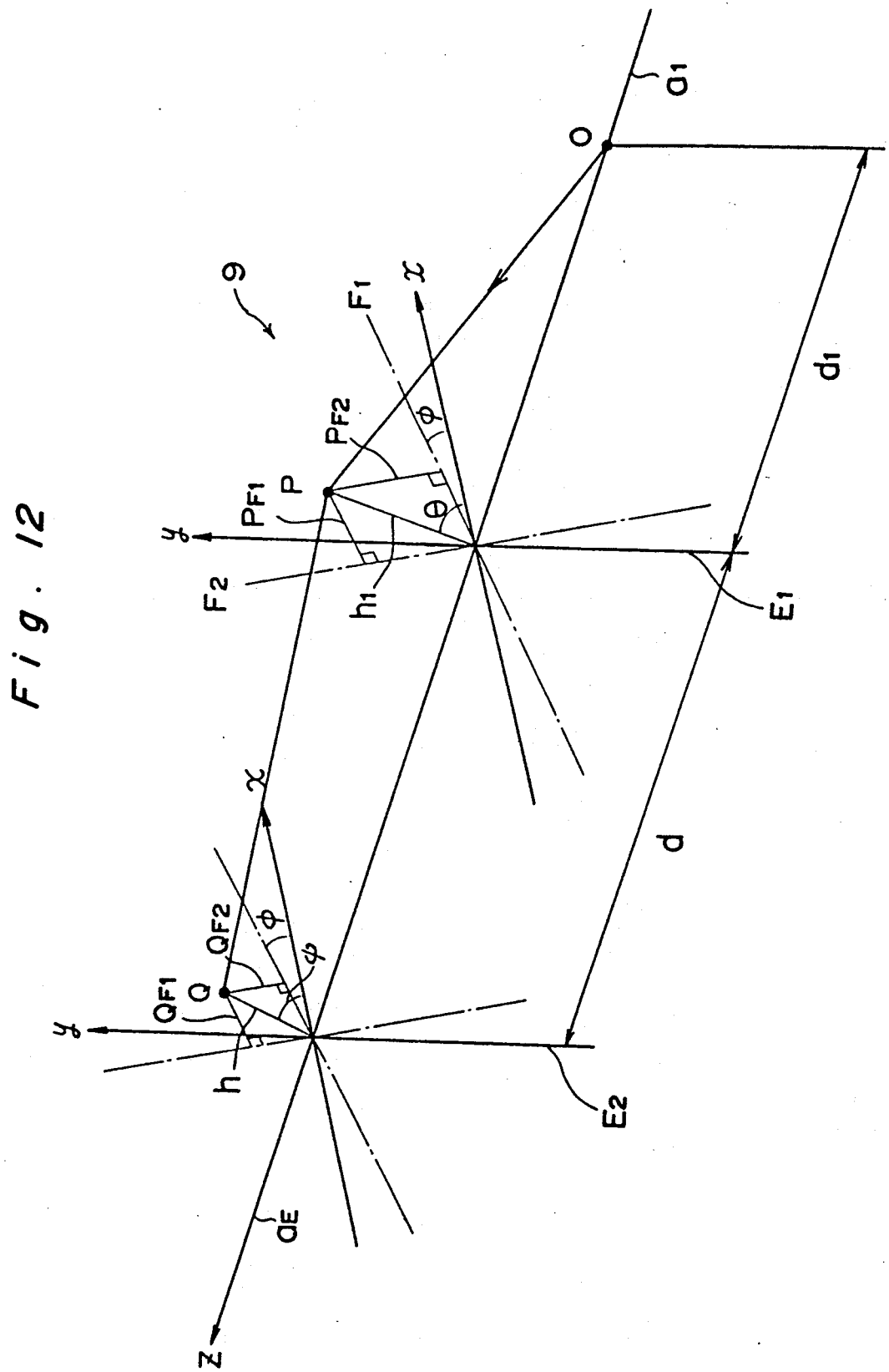
FIG. 12 is a perspective view showing an optical path through which a measuring light is incident on a cornea through a fixed point of the optical axis of the measuring light projecting optical system and then reaches a retina.

FIG. 12 shows an optical path in which the measuring light passes through a fixed point (O) disposed on the optical axis $a_1$, and then is incident on the retina $E_2$ through the cornea $E_1$. In FIG. 12, one measuring light is shown to represent all measuring lights. In the measuring light projecting optical system 9 in which optical axes-aligned and in-focus states are obtained, the optical axis $a_1$ thereof aligns with the optical axis $a_E$ of the eye on Z-axis and the measuring light passes through the fixed point (O) disposed on the optical axis $a_1$, then is incident on a point (P) on the cornea $E_1$, and thereafter reaches the point (Q) on the retina $E_2$. When the diaphragm 24 and the cornea are conjugate to each other with respect to the eyepiece 22 in the light receiving optical system 10, the measuring light projected by the light source 15 passes through the fixed point (O) on the optical axis $a_1$ through the eyepiece 22.

The following conditions are set in FIG. 12 in which the cornea $E_1$ is assumed to be the XY-plane. The distance between the retina $E_2$ and the cornea $E_1$ on the optical axis $a_E$, (d); the distance between the cornea $E_1$ and the fixed point (O), $d_1$; the distance between the point (P) on the cornea $E_1$ and the optical axis $a_E$, $h_1$; the angle formed by the intersection point at which the X-axis crosses Y-axis and the optical axis $a_E$ and the line drawn from the intersection point to the point (P), $\theta$; the angle which the major axis $F_1$ of an ellipse which indicates the refractive power of eye forms with X-axis, $\phi$; and the minor axis $F_2$ is at a right angle to the major axis $F_1$. Supposing that the component of the major axis direction is $P_{F1}$ and that of the minor axis $F_2$ is $P_{F2}$, $$P_{F1} = h_1 \cos(\theta - \phi) \quad (1)$$

$$P_{F2} = h_1 \sin(\theta - \phi) \quad (2)$$

The measuring light emitted by the light source 15 is refracted by the cornea. Thus, an image (point (Q)) is projected on the retina. The component $Q_{F1}$ of the major axis direction and the component $Q_{F2}$ of the minor axis direction are expressed as follows:

$$Q_{F1} = \left\{1 - d\left(\frac{1}{f1} - \frac{1}{d1}\right)\right\} \cdot P_{F1} \quad (3)$$

$$Q_{F2} = \left\{1 - d\left(\frac{1}{f2} - \frac{1}{d1}\right)\right\} \cdot P_{F2} \quad (4)$$

where 1/f1 is the refractive power of the cornea in the major axis direction thereof and 1/f2 is the refractive power of the cornea in the minor axis direction thereof.

Assuming that the refractive power $D_1$ of eye in the horizontal direction thereof and the refractive power $D_2$ of the eye in the vertical direction thereof are:

$$D_1 = \frac{1}{f1} - \frac{1}{d} \quad (5)$$

$$D_2 = \frac{1}{f2} - \frac{1}{d} \quad (6)$$

the equations (7) and (8) are given:

$$Q_{F1} = d\left(\frac{1}{d1} - D_1\right)h_1\cos(\theta - \phi) \quad (7)$$

$$Q_{F2} = d\left(\frac{1}{d1} - D_2\right)h_1\sin(\theta - \phi) \quad (8)$$

Figure 21:
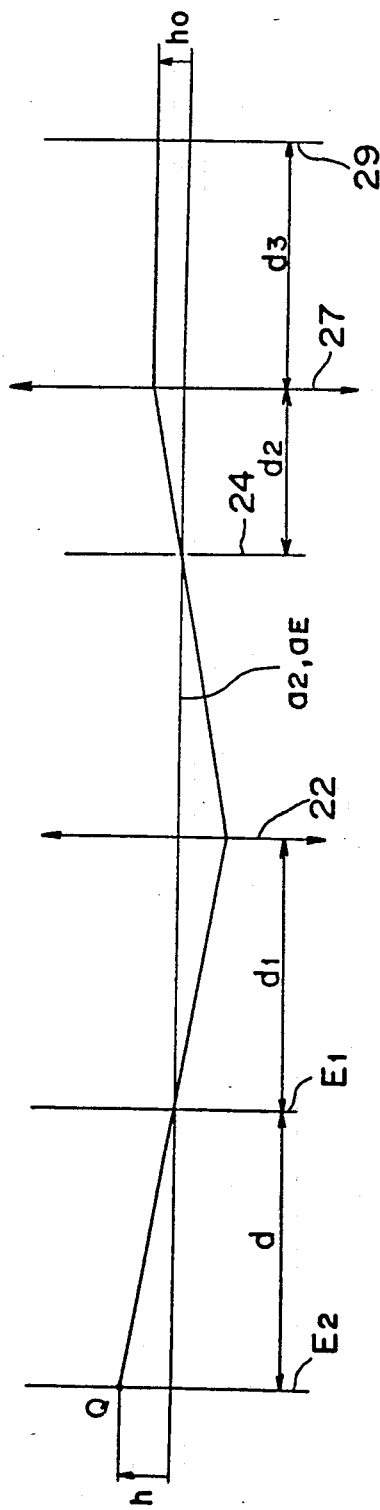
FIGS. 21 and 22 are views showing a measuring light receiving optical system and a measuring light projecting optical system, respectively for describing the method for correcting an error caused by the non-alignment between the optical axes of the measuring optical system and the eye shown in FIG. 1 through 15.

The image of the pattern projected on the retina viewed in the light receiving optical system 10 is shown in FIG. 21, the side elevational view, in which only beams in the vicinity of the optical axis of the light receiving system pass through the diaphragm 24 disposed in a position conjugate to the cornea $E_1$ with respect to the eyepiece 22, thus being incident on the image forming lens 27. The diaphragm 24 coincides with the focal point of the image forming lens 27. Therefore, the light of the pattern which has passed through the diaphragm 24 and is incident on the image forming lens 27 travels in parallel with the optical axis $a_2$. Thus, the light of the pattern projected on the retina forms an image on the light receiving sensor 29 with the distance of $h_0$ spaced from the optical axis $a_2$. That is, in the light receiving system, the image is formed on the retina $E_2$ in the height (h) from the optical axis and the light receiving sensor 29 detects that an image similar to the image formed on the retina $E_2$ is formed in the height of $h_0$ spaced from the optical axis $a_2$. Assuming that the angle formed by the intersection point at which the X-axis crosses Y-axis and the optical axis $a_E$ and the line drawn from the intersection to the point (Q), $\psi$; the angle which the major axis $F_1$ of an ellipse which indicates the refractive power of eye forms with X-axis, $\phi$; and the minor axis $F_2$ is at a right angle to the major axis. The relationship between (h) and ($h_0$) is expressed by the equation below.

$$\frac{h_0}{L} = \frac{h}{d} \quad (9)$$

where (L) is a constant determined by the focal points positions of the eyepiece 22 and the image forming lens 27. According to the above suppositions, $Q_{F1}$ and $Q_{F2}$ in the light receiving system are expressed by equations (10) and (11) below.

$$Q_{F1} = h \cos(\psi - \phi) \quad (10)$$

$$Q_{F2} = h \sin(\psi - \phi) \quad (11)$$

Substituting the relationship of the equation (9) for the equations (10) and (11), the following equations are obtained:

$$Q_{F1} = d \cdot \frac{h_0}{L} \cos(\psi - \phi) \quad (12)$$

$$Q_{F2} = d \cdot \frac{h_0}{L} \sin(\psi - \phi) \quad (13)$$

The equation (14) is established from the equations (7) and (12), and the equation (15) is given by the equations (8) and (13):

$$\frac{h_0}{L}\cos(\psi - \phi) = \left(\frac{1}{d1} - D_1\right)h_1\cos(\theta - \phi) \quad (14)$$

$$\frac{h_0}{L}\sin(\psi - \phi) = \left(\frac{1}{d1} - D_2\right)h_1\sin(\theta - \phi) \quad (15)$$

Transpositions and expansions are performed in the equations (14) and (15) assuming that $h_0 \cos\psi = Sx$ and $h_0 \sin \psi = Sy$ so as to obtain the coordinate (Sx, Sy) of the spot pattern detected by the sensor 29. Consequently, the coordinate is expressed by equations (16) and (17).

$$Sx = L \cdot h_1 \left(\frac{1}{d1} - D_1\right)h_1\cos(\theta - \phi)\cos\phi - \quad (16)$$

$$L \cdot h_1 \left(\frac{1}{d1} - D_2\right)\sin(\theta - \phi)\sin\phi$$

$$Sy = L \cdot h_1 \left(\frac{1}{d1} - D_1\right)\cos(\theta - \phi)\sin\phi + \quad (17)$$

$$L \cdot h_1 \left(\frac{1}{d1} - D_2\right)\sin(\theta - \phi)\cos\phi$$

Replacing $L \cdot h_1(1/d1 - D_1) = A$ with (A) and $L \cdot h_1(1/d1 - D_2) = B$ with (B) in the equations (16) and (17), these two equations are expressed as follows:

$$Sx = A\cos(\theta - \phi)\cos\phi - B\sin(\theta - \phi)\sin\phi \quad (18)$$

$$Sx = A\cos(\theta - \phi)\sin\phi - B\sin(\theta - \phi)\cos\phi \quad (19)$$

Unknown letters A, B, and $\phi$ in the equations (18) and (19) can be theoretically obtained by four equations which give coordinates Sx1, Sy1, Sx2, and Sy2 with respect to the two values $\theta_1$ and $\theta_2$ of $\theta$ determined by a projected pattern.

Sphere power (SPH), cylinder power (CYL), and cylinder axis (AXIS) indicated by $D_2$, $D_1 - D_2$, and $\phi$, respectively are used as the values for remedying an abnormal refractive power.

Figure 13:
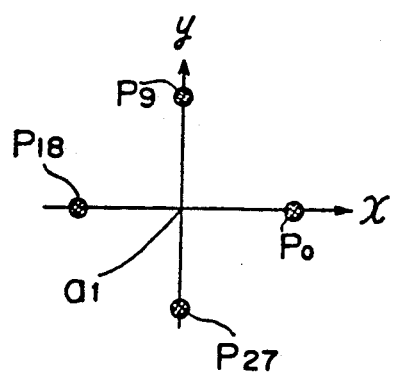
FIG. 13 is a view showing the positions of the spot pattern projected on a cornea on XY-plane.

As shown in FIG. 13, four spot patterns are used in this embodiment. Two spots are disposed on the horizontal and vertical lines thereof, respectively which are on the tangential plane of the cornea and pass through the optical axis $a_E$ of the eye (E) so that the optical axis $a_1$ ($a_E$) equally divides the distances between the two spots $P_0$ and $P_{18}$ on the horizontal line and the two spots $P_9$ and $P_{27}$ on the vertical line.

Solving the four equations shown above by supposing that the coordinate of the spot image $P_0$ ($\theta_1 = 0°$) on the light receiving sensor 29 is $Sx1 = Sxo$, $Sy1 = Syo$ and that the coordinate of the spot image $P_9$ ($\theta_2 = 90°$) is $Sx2 = Sx9$, $Sy2 = Sy9$, the following equations are obtained:

$$A = \tfrac{1}{2} \{S_{x0} + S_{y9} + \sqrt{(S_{x0} - S_{y9})^2 + 4S_{y0}^2}\} \quad (20)$$

$$B = \tfrac{1}{2} \{S_{x0} + S_{y9} - \sqrt{(S_{x0} - S_{y9})^2 + 4S_{y0}^2}\} \quad (21)$$

$$\phi = \tfrac{1}{2} \tan^{-1}\left(\frac{2 S_{y0}}{S_{x0} - S_{y9}}\right) \quad (22)$$

Accordingly, the refractive power of eye can be obtained by the image processing device 3 which detects the coordinates (Sz0, Sy0) and (Sx9, Sy9) of the spot images $S_0$ and $S_9$ formed on the light receiving sensor 29 which correspond to the two spot patterns $P_0$ and $P_9$ projected on the cornea $E_1$ shown in FIG. 13 which is a generalized coordinate of X-axis (horizontal direction) and Y-axis (vertical direction). The reason not two but four spot patterns are used in this embodiment will be described hereinbelow.

The distance $h_0$ of the spot image from the optical axis $a_2$ ($a_E$) formed on the light receiving sensor 29 is calculated by the following equation (refer to FIG. 21.)

$$h_0 = d_2 h_1 \left(\frac{1}{d1} - D\right) \quad (23)$$

where $d_2$ is the distance between the diaphragm 24 and the image forming lens 27.

The above equation (23) can be established on the assumption that the optical axis $a_E$ of the eye is aligned with the optical axis $a_2$ of the measuring system. But the equation (23) can be used if the optical axis $a_E$ of the eye is in non-alignment with the optical axis $a_2$ of the measuring optical system 8 in the range in which a paraxial theory can be applied. The use of the equation (23) causes no errors.

One of the reasons for using the equation 23 in the above case is that as described previously, the diaphragm having a slight aperture is disposed in the position conjugate to the cornea $E_1$ with respect to the eyepiece 22, the reason of which is described hereinbelow.

Figure 22:
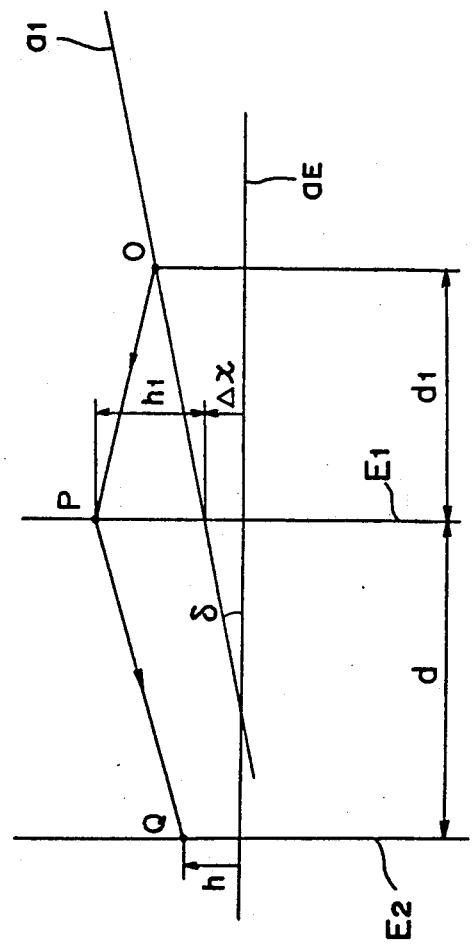

Referring to FIG. 22 showing the measuring light projecting system, if the angular error between the optical axis $a_1$ of the measuring system and the optical axis $a_E$ of the eye is δ(radian) and the rectilinear error between the two optical axes is Δx, the position or the height (h) of the spot image formed on the retina $E_2$ is shown by the following equation:

$$h = h_1 + \Delta x - d\left(\frac{h1 - \Delta x}{f} = \frac{h1}{d1} + \delta\right) \quad (24)$$

Figure 23:
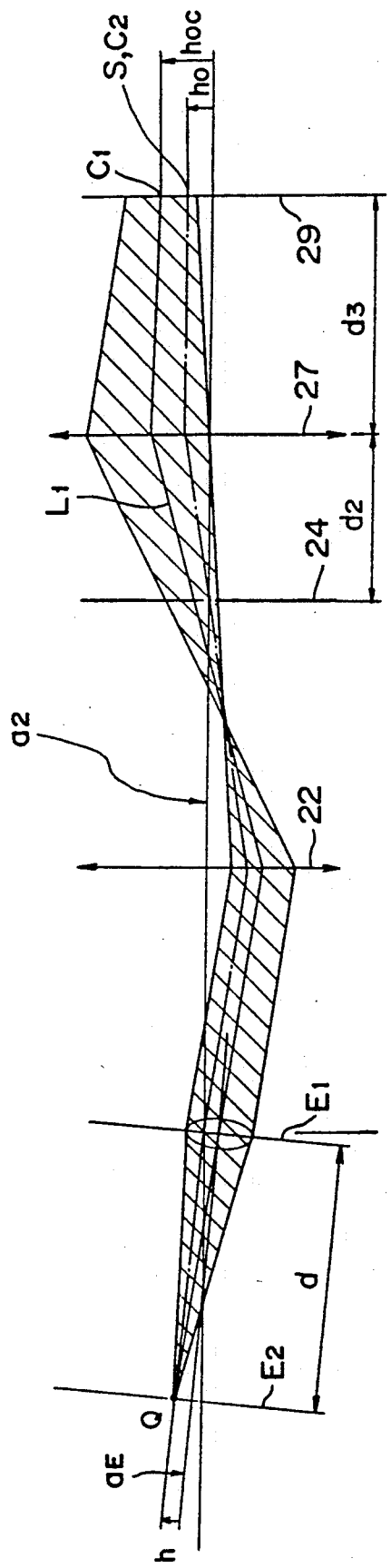
FIG. 23 is a view showing details of the measuring light receiving optical system shown in FIG. 21.

In this case, the light reflected from the retina $E_2$ is received by the measuring light receiving system 10 as shown in FIG. 23 which exaggeratingly shows the state in which the spot image having a certain area is detected by the sensor 29.

Supposing that, in FIG. 23, no diaphragm 24 is provided in the measuring light receiving optical system or that the aperture diameter of the diaphragm 24 is large, the area of the spot image formed on the light receiving sensor 29 is relatively great.

The center of gravity ($C_1$) corresponds to the projected point of a light which passes through the center of the pupil of the cornea $E_1$. Accordingly, the distance $h_{oc}$ of the center of gravity $C_1$ of the spot image from the optical axis $a_2$ of the light receiving optical system does not exactly correspond to the height (h) of the image (Q) formed on the retina $E_1$. That is, $$h_{oc} = \Delta x + d_2\left(\frac{\Delta x}{a} + \frac{h}{d} + \delta\right) - d_3 \cdot \frac{\Delta x}{d2} \quad (25)$$

The substitution of the equation 23 into the equation (25) gives the following equation.

$$h_{oc} = \Delta x d_2 \left(\frac{1}{d2} + \frac{1}{a} - D\right) + \quad (26)$$

$$d_2 h_1 \left(\frac{1}{d} - D\right) - d_3 \cdot \frac{\Delta x}{d2}$$

That is, the equation (26) includes the following error due to the non-alignment of the optical axes:

$$<\Delta x d_2 \left(\left(\frac{1}{d2} + \frac{1}{a} - D\right) - d_3 \cdot \frac{\Delta x}{d2}\right)>$$

In the above equation (26), $d_3$ represents the distance between the image forming lens 27 and the light receiving sensor 29; the focal length of the eyepiece 22 is (a); and the distance between the eyepiece 22 and the cornea $E_1$ and the distance between the eyepiece 22 and the diaphragm 24 is set to be 1:1.

As shown in FIG. 23, only light beams which have small diameters and pass through the intersection point of the optical axis $a_2$ of the measuring optical system 8 and the cornea $E_1$ can be formed on the light receiving sensor 29 by providing the optical axis $a_2$ of the light receiving system with the diaphragm 24 having a sufficiently small aperture.

Supposing that the light of the very small spot image received by the sensor 29 is (S) and the distance or the height of the center of gravity $C_2$ from the optical axis $a_2$ of the measuring light optical system is $h_0$, the following equation is established:

$$h_0 = d_2\left(\frac{\Delta x}{f} + \frac{h - \Delta x}{d} + \delta\right) \quad (27)$$

The following equation is given by substituting the equation (23) for the equation (27).

$$h_0 = d_2\left(\frac{h1}{d} - \frac{h1}{f} + \frac{h1}{d1}\right) = d_2 h_1 \left(\frac{1}{d1} - D\right) \quad (28)$$

The equation 28 not including an error due to the non-alignment of the optical axes is the same as the equation (23). The non-alignment between the optical axis of the eye and the optical axis of the measuring optical system 8 does not result in an erroneous measurement, i.e., the refractive power of eye can be correctly measured.

In addition to the above-described method, an error caused by the non-alignment between the optical axis of the light measuring optical system 8 and that of the eye can be also compensated by the following modified method.

Figure 24:
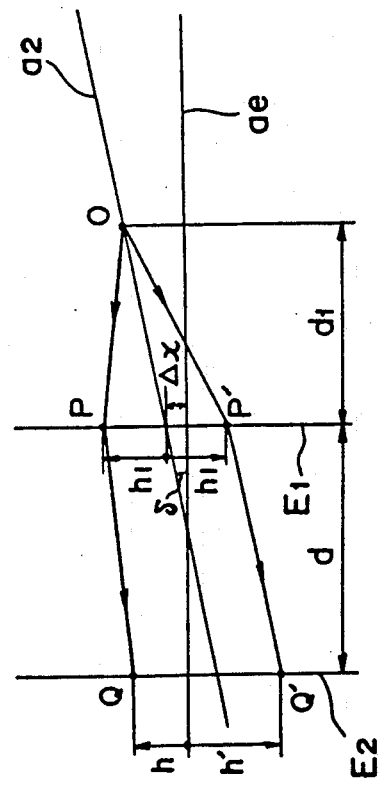
FIGS. 24 and 25 are views showing a measuring light projecting optical system and a measuring light receiving optical system by which a correcting method is performed in a manner different from the method shown in FIG. 21 through 23.

In the above-described embodiment, two pairs of spot lights are used as the measuring lights and the two spot lights of each of the pairs are disposed symmetrically with respect to the optical axis of the light measuring optical system 8. FIG. 24 shows an optical axes non-alignment of a pair of measuring lights.

The measuring lights are projected on points (Q) and (Q') of the retina $E_2$ through points (P) and (P') of the cornea $E_1$. The distances from the optical axis $a_2$ of the measuring optical system 8 to the point (P) and the point (P') are both ($h_1$), and the points (P) and (P') are symmetrical with respect to the optical axis $a_2$. That is, the distance between the point (P) and the optical axis $a_2$ is $h_1$, and the distance between the point (P') and the optical axis $a_2$ is ($-h_1$). The distances between the points (Q) as well as (Q') of the retina $E_1$ and the optical axis $a_E$ of the eye are (h) and (h'), respectively. In this condition, the following equations are obtained.

$$h = h_1 + \Delta x - d\left(\frac{h1 + \Delta x}{f} - \frac{h1}{d} - \delta\right) \quad (29)$$

$$h' = -h_1 + \Delta x - d\left(\frac{-h1 + \Delta x}{f} - \frac{-h1}{d} + \delta\right) \quad (30)$$

Figure 25:
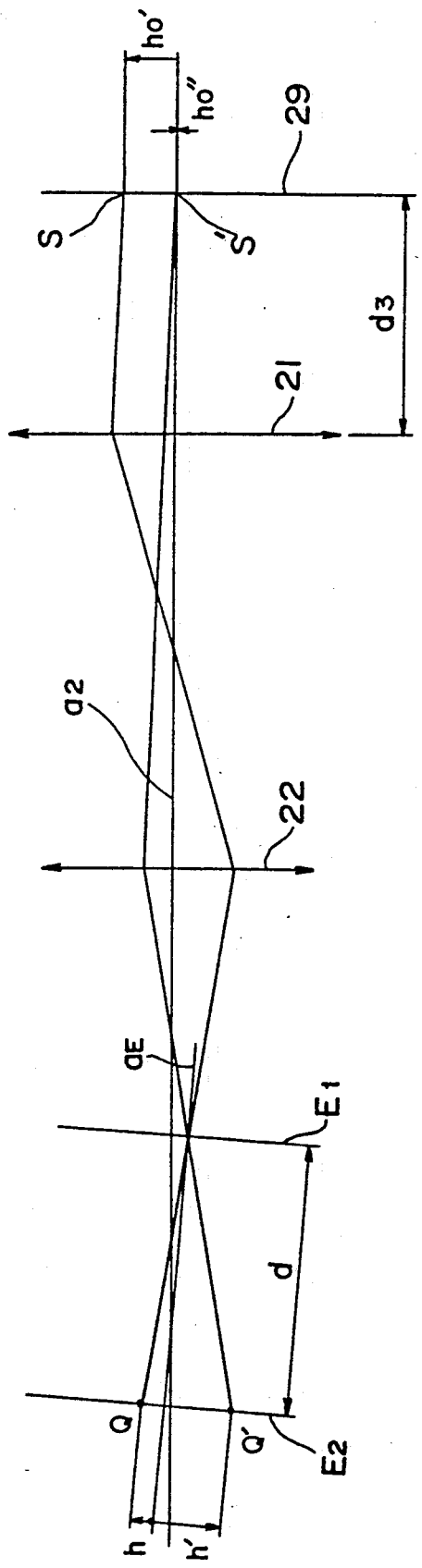

FIG. 25 shows the measuring light receiving optical system in this modification. The measuring light receiving optical system is not provided with a diaphragm.

Referring to FIG. 25, the lights of the two spot images formed on the retina $E_2$ at two points (Q) and (Q') thereof are supposed to form images S and S' on the light receiving sensor 29 through the cornea $E_1$, the eyepiece 22, and the image forming lens 27. Of the lights of the two spot images formed on the points (Q) and (Q') of the retina $E_2$, only the light beams which pass through the center of the pupil of the cornea $E_1$ are shown for consideration. In this case, the light beams correspond to the centers of gravity of the spot images (S) and (S').

Assuming that the positions or the heights of the centers of gravity of the spot images (S) and (S') from the optical axis $a_2$ are $h_0'$ and $h_0''$, the following equations are obtained:

$$h_0' = \Delta x + d_2\left(\frac{\Delta x}{a} + \frac{h}{d} + \delta\right) - d_3 \cdot \frac{\Delta x}{d2} \quad (31)$$

$$h_0'' = \Delta x + d_2\left(\frac{\Delta x}{a} + \frac{h'}{d} + \delta\right) - d_3 \cdot \frac{\Delta x}{d2} \quad (32)$$

Substituting the equation 29 for the equation 31 and the equation 30 for the equation 32, the following equations are established.

$$h_0' = \Delta x\left\{1 + d_2\left(\frac{1}{a} - D\right)\right\} + \quad (33)$$

$$d_2 h_1 \left(\frac{1}{d1} - D\right) - d_3 \cdot \frac{\Delta x}{d2}$$

$$h_0'' = \Delta x\left\{1 + d_2\left(\frac{1}{a} - D\right)\right\} - \quad (34)$$

$$d_2 h_1 \left(\frac{1}{d1} - D\right) - d_3 \cdot \frac{\Delta x}{d2}$$

Considering that the spot images (S) and (S') formed on the sensor 29 correspond to the points (Q) and (Q') shown in FIG. 24 showing the measuring light projecting optical system, the distance or the height ($h_0$) of the spot images (S) and (S') formed on the sensor 29 are given by the following equation:

$$h_0 = \frac{h_0' - h_0''}{2} \quad (35)$$

Substituting the equations (33) and (34) for the equation (35), the following equation is obtained:

$$h_0 = \frac{h_0' - h_0''}{2} \quad (36)$$

$$= d_2 h_1 \left(\frac{1}{d1} - D\right)$$

The equation 36 does not include error amounts $\Delta x$ and $\delta$ due to the non-alignment between the optical axes of the measuring optical system 8 and the eye. That is, a measured value having no errors can be automatically obtained.

In the above description, only a pair of the measuring lights is used to calculate the height $H_0$. Similarly, the other height $h_0$ can be obtained by using another pair of the measuring lights in the same manner as described above.

In this modification, a pair of measuring lights are used to measure the heights ($h_0'$) and ($h_0''$) of the spot images, whereby the height ($h_0$) are obtained according to the equation (35).

Preferably, the two methods for correcting the error due to the non-alignment of the optical axes described above are adopted in combination thereof. A diaphragm having a sufficiently small aperture is used according to the first method. But needless to say, it is necessary that the aperture be large enough to allow the passage of a light beam having a predetermined amount of quantity so as to correspond to the resolving power of the sensor 29. The smaller the area of a spot image formed on the sensor 29 is, the more accurate the position of the center of gravity of the spot image is. On the other hand, in proportion to the increase of the area of the spot image, the position of the center of gravity of the spot image calculated becomes less accurate. According to the second method, the area of the spot image formed on the sensor 29 is considerably great because a diaphragm is not mounted on the measuring light receiving optical system, which necessitates the provision of a sensor having a very great light receiving area. Thus, the second method makes it difficult to manufacture a compact apparatus for measuring the refractive power of eye.

Figure 26:
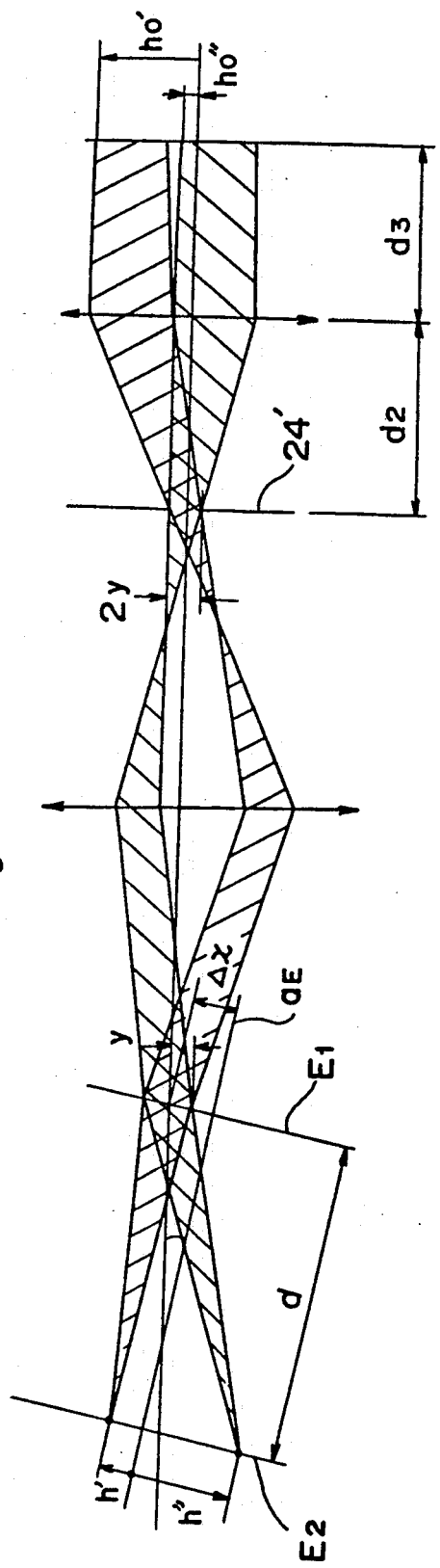
FIG. 26 is a view showing a measuring light receiving optical system in which the correcting method shown in FIGS. 21 and 22 and the correcting method shown in FIGS. 24 and 25 are simultaneously performed.

In order to overcome the disadvantages of the first and second methods, both methods are preferably used in combination. That is, in the first method, the diameter of the aperture of the diaphragm 24 is made as small as possible to allow a sufficient amount of light beam to pass therethrough toward the sensor 29. In this condition, the second method is utilized. FIG. 26 shows the measuring light receiving optical system of a third method in which both the first and second methods are simultaneously carried out. FIG. 26 shows one of the lights which passes on the upper edge portion of the aperture of the diaphragm 24' in order to make it easy to understand the third method. FIG. 26 is similar to FIG. 25 except that a diaphragm 24' is mounted on the measuring light receiving optical system and that the lights reflected from the retina on which a spot image is formed is exaggeratingly shown as a light beam. In this light receiving optical system, the radius of the aperture of the diaphragm 24' is (y).

Supposing that the measuring light projecting optical system shown in FIG. 24 projects measuring lights to the eye, the following equation is established with regard to a first one of a pair of the measuring lights.

$$h_0' = y + d_2 \left\{ \frac{y}{a} + \frac{1}{f}(\Delta x - y) + \frac{1}{d}(h - \Delta x + y) + \delta \right\} - d_3 \cdot \frac{y}{d2} \quad (37)$$

Substituting the equation (29)

$$h = h_1 + \Delta x - d\left(\frac{h_1 + \Delta x}{f} - \frac{h_1}{d} + \delta\right)$$

for the equation (37), the following equation is obtained.

$$h_0' = y + d_2 \left\{ \frac{y}{a} + \frac{1}{f}(\Delta x - y) + \frac{1}{d}(h_1 + \Delta x) - \frac{1}{f}(h_1 + \Delta x) + \frac{h_1}{d1} - \frac{1}{d}(\Delta x - y) \right\} - d_3 \cdot \frac{y}{d2} \quad (38)$$

Similarly, regarding a second one of a pair of the measuring lights, the following equation is obtained.

$$h_0'' = y + d_2 \left\{ \frac{y}{a} + \frac{1}{f}(\Delta x - y) + \frac{1}{d}(h' - \Delta x + y) + \delta \right\} - \quad (39)$$

-continued $$d_3 \cdot \frac{y}{d2}$$

As described above, the following equation is found from the equation (30).

$$h' = -h_1 + \Delta x - d\left(\frac{-h_1 + \Delta x}{f} - \frac{-h_1}{d1} + \delta\right) \quad (40)$$

The following equation is obtained by substituting the equation (40) for the equation (38).

$$h_0'' = y + d_2 \left\{ \frac{y}{a} + \frac{1}{f}(\Delta x - y) + \frac{1}{d}(-h_1 + \Delta x) - \frac{1}{f}(-h_1 + \Delta x) + \frac{-h_1}{d1} - \frac{1}{d}(\Delta x - y) \right\} - d_3 \cdot \frac{y}{d2} \quad (41)$$

The following equation (42) obtained by diving the remainder found by performing the subtraction between $h_0'$ and $h_0''$ does not include the error $\Delta x$ and $\delta$.

$$h_0 = \frac{h_0' - h_0''}{2} = d_2 \left( \frac{1}{d} h_1 - \frac{1}{f} h_1 + \frac{1}{d1} h_1 \right) = d_2 h_1 \left( \frac{1}{d1} - D \right) \quad (42)$$

The equations (37) and (38) are general equations. Assuming that y=0, i.e., considering the light which passes through the center of the aperture of the diaphragm, the equation obtained in this case equals to the equations (33) and (34).

The method for compensating the error caused by the non-alignment between the optical axes of the measuring optical system 8 and the eye is described above, however, the error compensation can be made only when the error between both optical axes is small, i.e., compensated only in the range, for example, $\Delta x < \pm 1$ mm and $\delta < \pm 10°$, to which the paraxial theory is applicable. If the optical axes nonalignment-caused error exceeds the error range, the error cannot be compensated because a spot image formed on the light receiving sensor is distorted by the influence of aberration. That is, even though the error is compensated, a calculated value is not reliable. In this case, a processing for the error is performed because the calculated value is not reliable. The error processing is described with reference to the flowcharts shown in FIG. 15.

The operation of the apparatus for measuring the refractive power of eye is described with reference to the flowcharts shown in FIG. 15A, 15B, 15C, and 15D.

First, at #step 100, the microcomputer goes into a preparation mode, i.e., the illuminating light source 30 and the reticle light source 35 are ON, and the measuring light projecting light source 15 is OFF. Then, the program goes to step #101. At this time, if there is the eye (E) forward of the illuminating light source 30, the light of spots reflected from the cornea and the reticle pattern are displayed on the monitor screen, and if there is no eye forward of the illuminating light source 30, only the reticle pattern is displayed on the monitor screen. At step #100, a timer interruption is allowed from step #100'. At step #100', the image information on the eye is periodically inputted to the memory of the microcomputer 5 in order to automatically monitor the eye. To this end, the state in which only the illuminating light source 30 is ON and the reticle light source 35 and the illuminating light source 15 are both OFF is created for a moment. If there is an eye (E) forward of the illuminating light source 30 at this moment, the image of the eye (E) is recorded, whereby the state of the eye (E) (state of spots reflected from the cornea) is detected. At step #100', in order to control periodically the condition of the switch 6 which sets the conditions of the calculation and the control, the condition of the switch 6 is detected. If a change is detected in the input to the switch 6, the content stored in the memory for storing the condition of the switch 6 of the microcomputer 5 is updated at step #100'.

At step #101, it is decided whether or not the switch of the printer 7 is ON. If the switch is ON, the data previously stored by the microcomputer 5 is outputted to the printer 7 at step #102. If the switch is OFF at step #101, the program goes to step #103.

At step #103, it is decided whether or not the eye (E) is in front of the illuminating light source 30. If yes, the program goes to step #104. If no, the program returns to step #100 from which operations are performed at each step. This decision is made according to whether or not the illuminating light reflected from the cornea is formed on the light receiving sensor 29. The examiner can check this through the monitor screen as well.

At step #104, the microcomputer 5 goes into the optical axes alignment detecting mode, i.e., the image processing device 3 finds the position of the center of gravity of spot images of the illuminating light reflected from the cornea, namely, the coordinate ($x_0$, $y_0$) of the center of the circle in X-axis and Y-axis formed by spot images. Thereafter, the program goes to step #105.

It is decided at step #105 whether or not the absolute value $|x_0|$ of X-coordinate ($x_0$) obtained at step #104 is smaller than the reference X-axis non-alignment value set as the allowable range of the non-alignment in X-axis direction. If the absolute value $|x_0|$ is smaller than the reference value, the program goes to step #106 and if not smaller, the program returns to step #100. Then, operations are performed from step #100 through step #105.

It is decided at step #106 whether or not the absolute value $|y_0|$ of Y-coordinate ($y_0$) calculated at step #104 is smaller than the reference Y-axis non-alignment value set as the allowable range of the non-alignment in Y-axis direction. If the absolute value $|y_0|$ is smaller than the reference value, the program goes to step #107 and if not smaller, the program returns to step #100. Then, operations are performed from step #100 through step #106.

At step #107, the microcomputer 5 goes into the in-focus state detecting mode, i.e., the image processing device 3 detects the high frequency component (Hf) of the image signal of the spots of the illuminating light reflected from the cornea, then the program goes to step #108. This method for detecting the in-focus state by detecting the high frequency component is one example of the methods which can be achieved by only a software, however, in general, the in-focus state can be detected by detecting the contrast of spot pattern in combination of the function of a hardware.

At step #108, it is decided whether or not the value of the high frequency component (Hf) found at step #107 is greater than the value of the contrast reference set as the allowable range of the in-focus state. If the value of the frequency component (Hf) is greater than that of the contrast reference, the program goes to step #109 and if not greater, the program returns to step #100. Then, operations are performed from step #100 through step #108.

The result of the optical axes alignment and in-focus detecting operations performed at step #104 through step #107 appears on the monitor in the uncoincidence between the reticle pattern and the spots and the difference in the contrast among the spots. Therefore, the examiner can check the optical axes alignment and in-focus detecting conditions according to the monitor screen.

At step #109, the microcomputer 5 goes into an angle compensating mode. Of illuminating lights of spots reflected from the cornea, only the illuminating light sources corresponding to two spots on the reference diameter 42 is ON and the other illuminating light source, namely, four illuminating light sources 30, the light source 15 which emits the measuring light and the reticle light source 35 are OFF. The data of this condition is inputted to the monitor 4. Then, the program goes to step #110.

At step #110, the microcomputer 5 detects the angle α which the straight line formed by connecting two spots forms with the horizontal reference line corresponding to the horizontal axis of the optical measuring device 1 shown on the monitor 4. Thereafter, the program goes to step #111.

At step #111, the microcomputer 5 goes into a measuring mode, that is, the illuminating light source 30 and the reticle light source 35 are turned OFF and the measuring light projecting light source 15 is turned ON. The data of this condition is inputted to the monitor 4, then the program goes to step #112. At this time, the monitor 4 temporarily displays the pattern of the image formed on the retina and detected by the light receiving sensor 29 of the measuring light receiving optical system 10. Thus, the examiner completes the examination of the eye. Therefore, the program immediately returns to step #100 at which the microcomputer goes into the preparation mode, i.e., the light source 15 is OFF, and the illuminating light source 30 and the reticle light source 35 are ON.

Then, the program goes to step #113 at which it is decided whether or not the level of a signal inputted to the light receiving sensor 29 of the measuring light receiving optical system 10 is sufficient. This is because if the patient has a cataract, the level of the image signal detected by the light receiving sensor 29 may not be appropriate for measuring the refractive powers of his eyes. If it is decided at step #113 that the signal level is sufficient, the program goes to step #114 at which the microcomputer 5 goes into a calculation mode and if it is decided at step #113 that the signal level is insufficient, the program goes to step #120 at which an error processing is performed. In order perform the processing for the error at this step, for example, "no target" is displayed on the monitor screen at step #116 which is described later.

At step #114, based on the data of a measured result inputted to the microcomputer 5, the microcomputer 5 calculates the following with reference to the operation expression previously stored therein: the sphere power (SPH), cylinder power (CYL), cylinder axis (AXIS) which are the elements of the lens for glasses or a contact lens are calculated. The operation expressions of these elements are different from each other because points to be measured vary depending on light projective patterns. In this embodiment, four spot patterns spaced from each other at an angular interval of 90° are projected to the eye.

Figure 14:
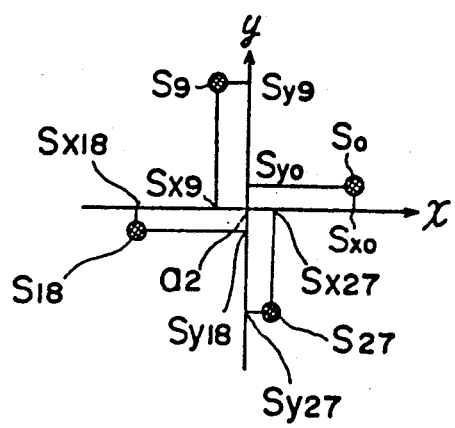
FIG. 14 is a view showing the positions of spot pattern on a light receiving sensor corresponding to the spot pattern projected on the cornea as shown in FIG. 13.

As shown in FIG. 14, the X-coordinates and Y-coordinates of spots $S_0$ ($S_{x0}$, $S_{y0}$), $S_9$ ($S_{x9}$, $S_{y9}$), $S_{18}$ ($S_{x18}$, $S_{y18}$), and $S_{27}$ ($S_{x27}$, $S_{y27}$) are found to obtain sphere power (SPH), cylinder power (CYL), and cylinder axis (AXIS) according to the following calculation.

$$Sx1 = \frac{Sx0 - Sx18}{2}$$

$$Sx2 = \frac{Sx27 - Sx9}{2}$$

$$Sy1 = \frac{Sy0 - Sy18}{2}$$

$$Sy2 = \frac{Sy27 - Sy9}{2}$$

$$A = \frac{1}{2}\left[S_{x1} + S_{y2} + \sqrt{(S_{x1} - S_{y2})^2 + 4S_{y1}^2}\right]$$

$$B = \frac{1}{2}\left[S_{x1} + S_{y2} - \sqrt{(S_{x1} - S_{y2})^2 + 4S_{y1}^2}\right]$$

$$SPH = D_2 = \frac{1}{d1} - \frac{1}{L \cdot h1} \cdot B$$

$$CYL = D_1 - D_2 = \frac{1}{L \cdot h1}(B - A)$$

$$AXIS = \phi - \alpha = \frac{1}{2}\tan^{-1}\left(\frac{2Sy1}{Sx1 - Sy2}\right) - \alpha$$

After performing the above operations, the program goes to step #115.

Figure 15A:
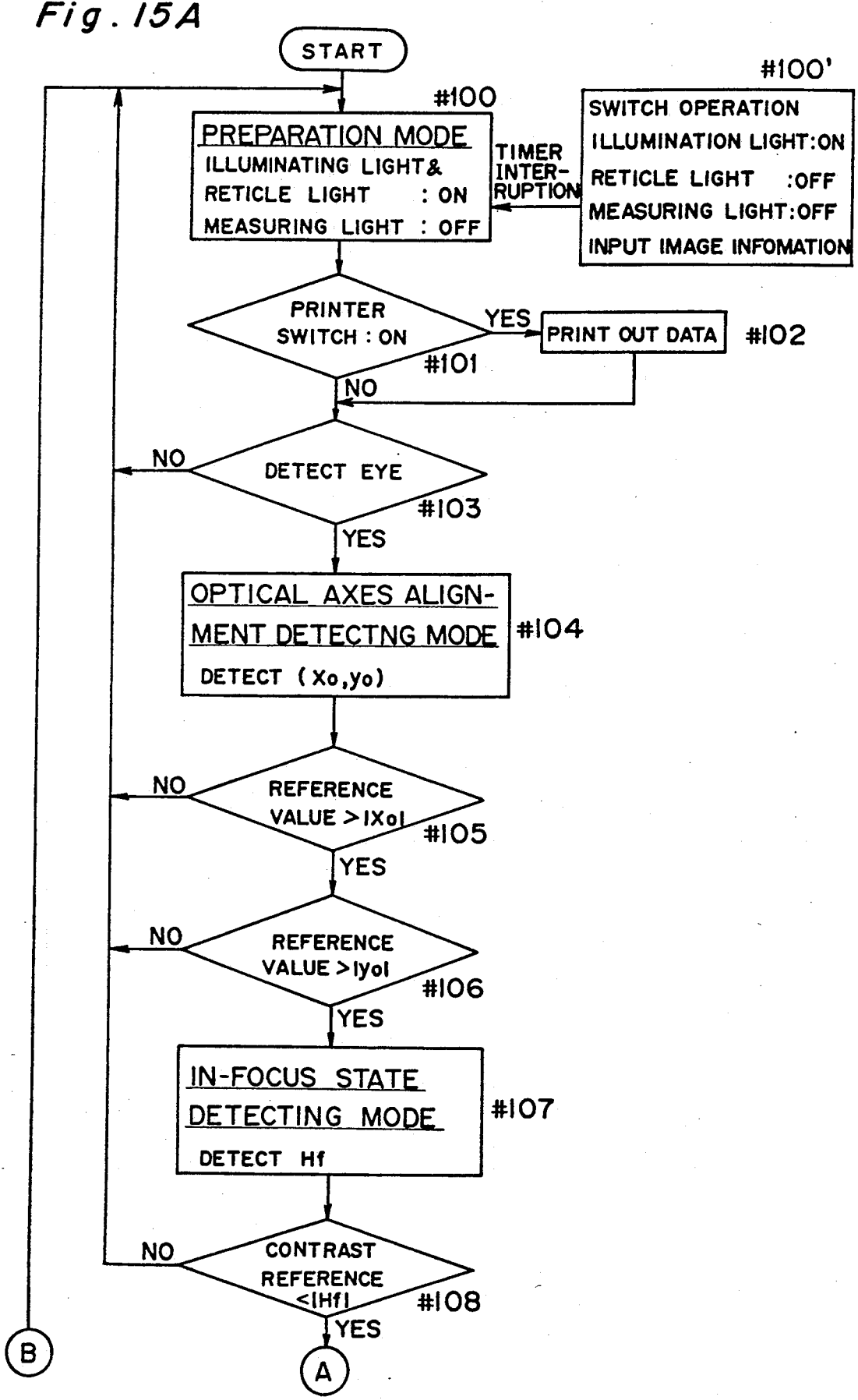
FIG. 15A, 15B, 15C, and 15D are flowcharts showing the operation to be effected in measuring the refractive power of eye.
Figure 15B:
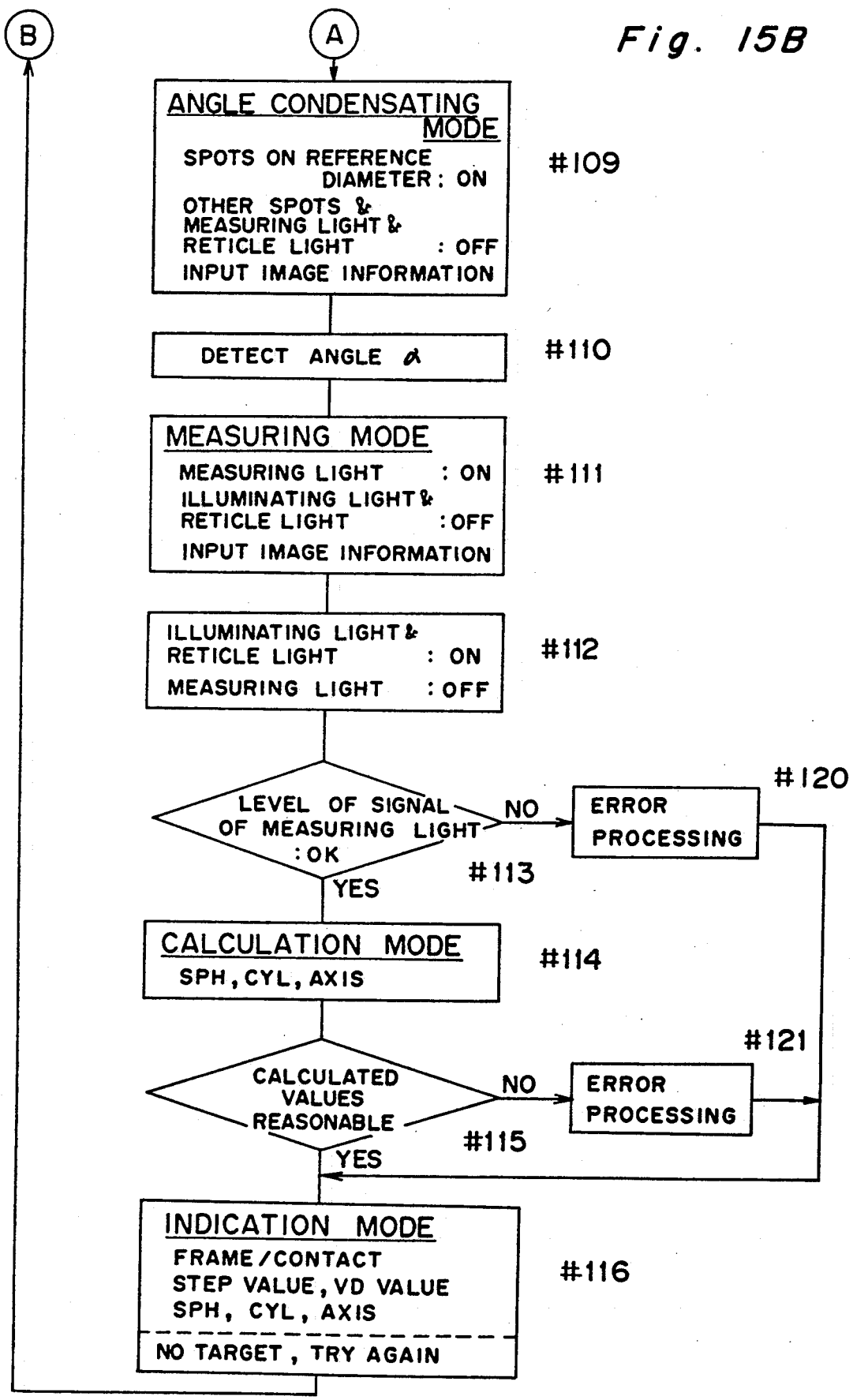
Figure 15C:
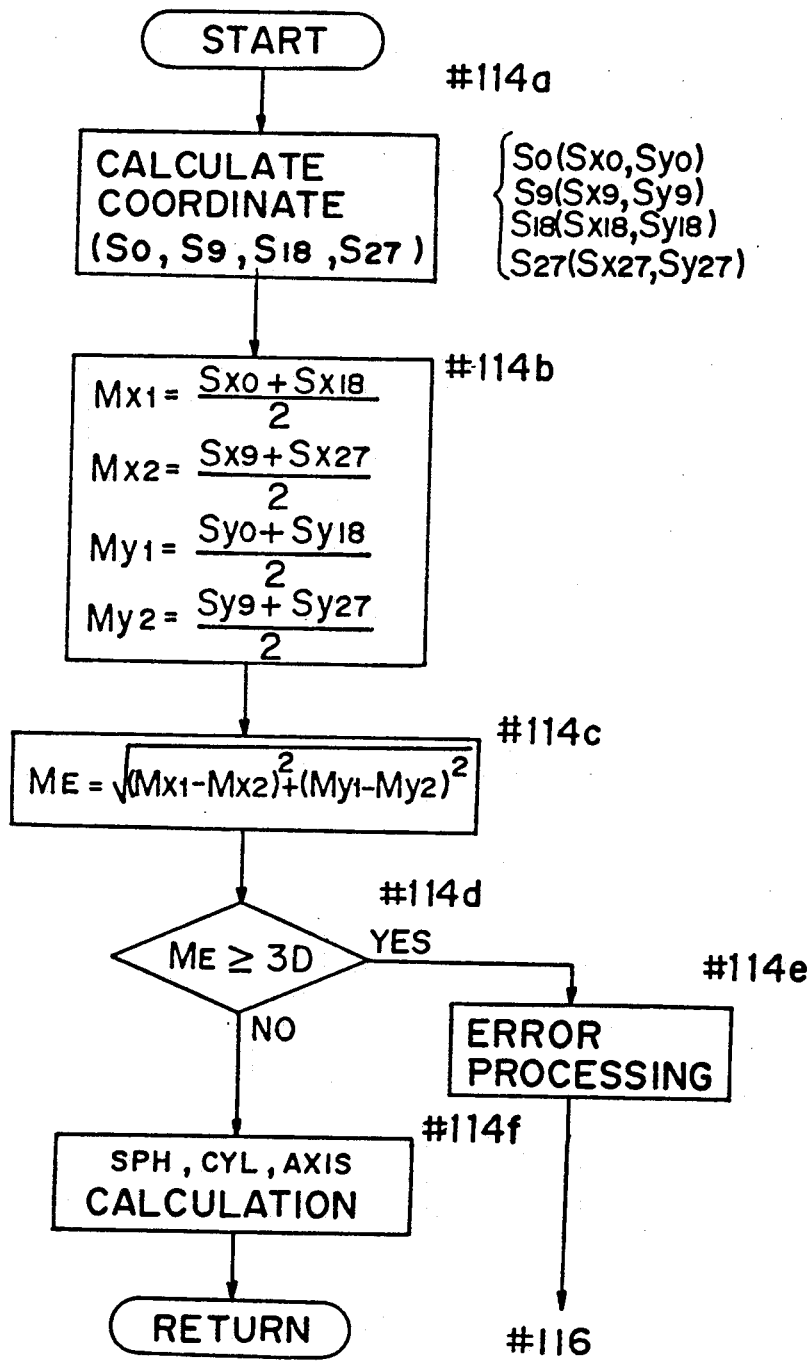
Figure 15D:
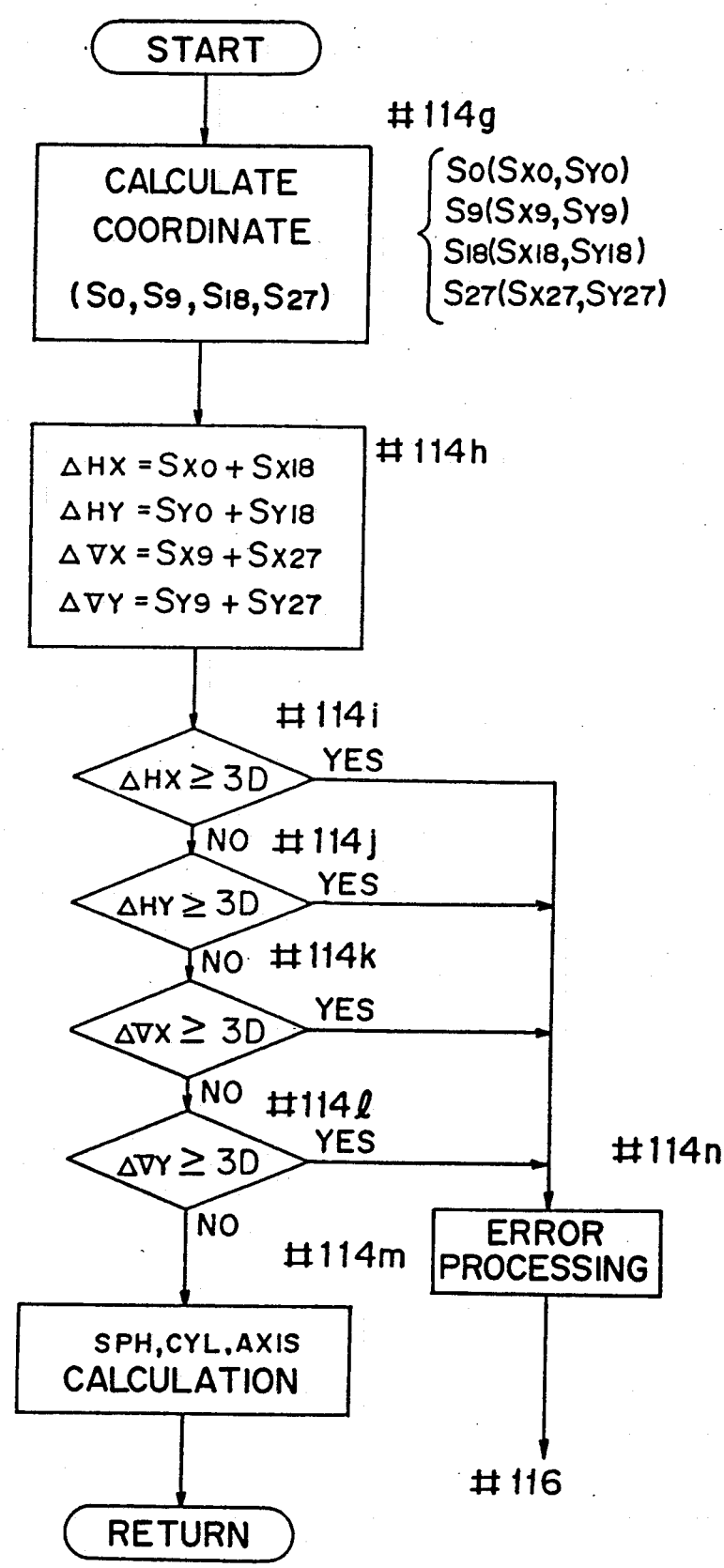

FIG. 15C shows the subroutine to which the program goes from step #114. In this subroutine, a processing for an error is performed. When the optical axis of the eye becomes non-aligned with that of the measuring optical system 8 between the time optical axes aligned and in-focus states are obtained and the time the measuring light is projected to the eye, data obtained is not reliable. That is, since hand-movable measuring optical measuring device 1 is used, it is likely to be shaken by hand. But owing to the subroutine shown in FIG. 15C, the shake can be checked.

This subroutine is described with reference to FIGS. 15C and 27A.

Figure 27A:
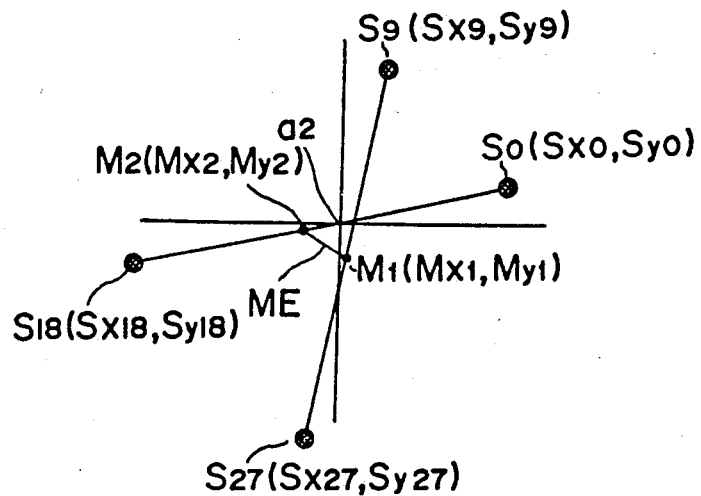
FIGS. 27A and 27B are explanatory views showing methods for performing an error processing.

FIG. 27A shows the coordinates of four spot images $S_0$, $S_9$, $S_{18}$, and $S_{27}$ which are detected by the image processing device 3 when the optical axis of the eye comes to be in non-alignment with the optical axis of the measuring light optical system between the time optical axes-aligned and in-focus states are obtained and the time the measuring light is projected to the eye.

First, at step #114a, the coordinate $S_0$ ($S_{x0}$, $S_{y0}$), $S_9$ ($S_{x9}$, $S_{y9}$), $S_{18}$ ($S_{x18}$, $S_{y18}$), and $S_{27}$ $S_{x27}$, $S_{y27}$) of the center of gravity of each of the spot images $S_0$, $S_9$, $S_{18}$, and $S_{27}$ are detected.

Next, at step #114b, the middle point of a pair of spots $S_0$ and $S_{18}$ and that of a pair of spots $S_9$ and $S_{27}$ are calculated. For example, the middle point $M_1$ ($M_{x1}$, $M_{y1}$) of the spot images $S_9$ and $S_{27}$ and the middle point $M_2$ ($M_{x2}$, $M_{y2}$) of the spot images $S_0$ and $S_{18}$ are calculated as follows:

$$Mx1 = \frac{Sx0 + Sx18}{2}$$

$$Mx2 = \frac{Sx9 + Sx27}{2}$$

$$My1 = \frac{Sy0 + Sy18}{2}$$

$$My2 = \frac{Sy9 + Sy27}{2}$$

Next, at step #114c, the distance ME ($=|M_1M_2|$) from the middle point $M_1$ ($M_{x1}$, $M_{y1}$) to the middle point $M_2$ ($M_{x2}$, $M_{y2}$) is calculated by the following equation.

$$ME = \sqrt{\{(Mx1 - Mx2)^2 + (My1 - My2)^2\}}$$

The distance ME is zero when the optical axis of the eye aligns with that of the measuring optical system 8, and becomes greater as the non-alignment amount between both optical axes becomes great. When the non-alignment amount between both optical axes is great, a measured value is not reliable. In this embodiment, "three diopters" is adopted as a reference value so as to decide whether or not the measured value is reliable. If it is detected at step #114d that the distance ME is more than three diopters, the program goes to step #114e at which the processing for the error is performed. Then, the program goes to step #116. At step #116, "Try again" is, for example, displayed on the monitor screen as the error processing, which is described later. If it is detected at step #114d that the distance ME is less than three diopters, the measure value is reliable. In this case, the program goes to step #114f at which similarly to the calculation to be performed at step #114, a sphere power (SPH), a cylinder power (CYL), and a cylinder axis (AXIS) are calculated.

As described above, the non-alignment amount between the optical axes of the measuring optical system 8 and the eye is detected by calculating the positions of the four spot images relative to the optical axis of the measuring light receiving optical system. In addition, the positions of the four spot images relative to the optical axis of the measuring light receiving optical system can be detected by a different method. This method is described hereinbelow with reference to the subroutine shown in FIG. 15D and FIG. 27B.

Figure 27B:
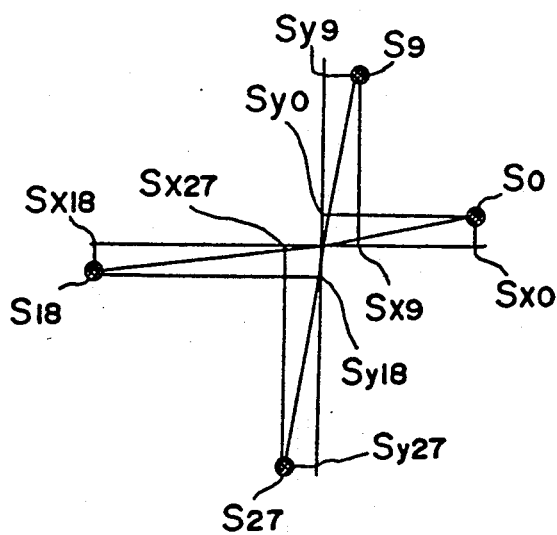
Figure 28:
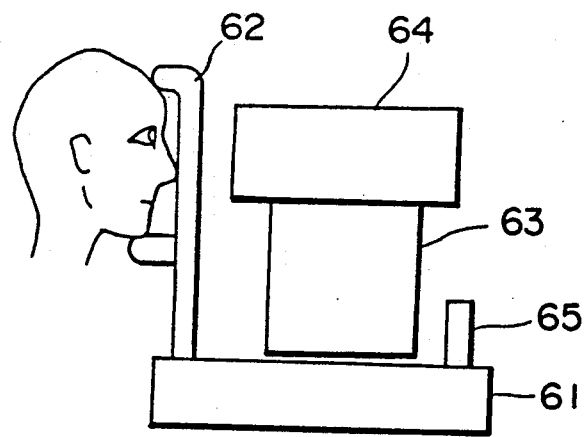
FIG. 28 is a side elevational view showing a known apparatus for measuring the refractive power of eye, as previously described.

FIG. 27B is similar to FIG. 27A. First, at step #114g, the coordinates of the centers of gravity $S_0$ ($S_{x0}$, $S_{y0}$), $S_9$ ($S_{x9}$, $S_{y9}$), $S_{18}$ ($S_{x18}$, $S_{y18}$), and $S_{27}$ ($S_{x27}$, $S_{y27}$) of spot images $S_0$, $S_9$, $S_{18}$, and $S_{27}$ are detected.

At step #114h, the following values are calculated by the equations shown below: The difference $\Delta Hx$ between the coordinates of the spot images of $S_0$ and $S_{18}$ in X-axis direction; the difference $\Delta Hy$ between the coordinates of the spot images of $S_0$ and $S_{18}$ in Y-axis direction; the difference $\Delta Vx$ between the coordinates of the spot images of $S_9$ and $S_{27}$ in X-axis direction; and the difference $\Delta Vy$ between the coordinates of the spot images of $S_9$ and $S_{27}$ in Y-axis direction.

$$Hx = Sx0 + Sx18$$

$$Hy = Sy0 + Sy18$$

$$Vx = Sx9 + Sx27$$

$$Vy = Sy0 + Sy27$$

Next, at steps #114*i*, #114*j*, #114*k*, and #114*l*, the differences ΔHx, ΔHy, ΔVx, and ΔVy are compared with the reference value, namely, three diopters, respectively.

If it is detected at the respective steps that the difference therebetween are not greater than the reference value, the program goes from step #114*i* to step #114, then from step #114*l* to step #114*m*. If it is detected at step #114*i* through step #114 that the differences therebetween are greater than the reference value, the program goes to step #114*n* at which error processings are performed. At step #114*m*, an operation similar to that to be performed at step #114*f* is carried out.

Another method for detecting the non-alignment amount between the optical axes of the eye and the measuring optical system 8 is described hereinbelow. The distance between the coordinates of the centers of gravity of the spot image $S_0$ ($S_{x0}$, $S_{y0}$) and $S_9$ ($S_{x9}$, $S_{y9}$) and the distance between the coordinates of the centers of gravity of the spot image $S_{18}$ $S_{x18}$, $S_{y18}$) and $S_{27}$, ($S_{x27}$, $S_{y27}$) are compared with each other or the distance between the coordinates of the centers of gravity of the spot image $S_0$ ($S_{x0}$, $S_{y0}$) and $S_{27}$ ($S_{x27}$, $S_{y27}$) and the distance between the coordinates of the centers of gravity of the spot image $S_9$ ($S_{x9}$, $S_{y9}$) and $S_{18}$ ($S_{x18}$, $S_{y18}$) are compared with each other.

The operation to be performed at step #115 and the operations to be performed at steps subsequent thereto are described hereinbelow. It is detected at step #115 whether or not the values of the sphere power (SPH), cylinder power (CYL), and the cylinder axis (AXIS) are in a reasonable range, respectively. If it is decided that the values are in the reasonable range, the program goes to step #116. If it is decided that the values are not in the reasonable range, the program goes to step #121 at which error processings are performed. One example of the displays of the error processing is "try again" which is made at step #116 on the monitor screen, which is described later.

At step #116, the calculation performed at step #114 or the display according to the error processings performed at steps #120 or #121 are displayed on the monitor screen. As the output condition for displaying the result of the calculation performed at step #116, the following displays can be made. For example, the display of a lens for glasses can be changed to the display for a contact lens. In addition, it is possible to set the display mode of the values obtained by the calculation, namely, step value or a unit by which the displayed value is altered. These displays are made by operating switches at step #100 so as to input necesarry information to the microcomputer 5. Further, it is possible to set the distance (VD value) between the lens for the glasses and the cornea. The VD value is zero in the case of the contact lens. When the operation to be performed at step #116 is terminated, the program returns to step #100 at which the microcomputer 5 goes into the preparation mode.

The measuring optical system 8 shown in FIG. 2 through FIG. 8 is one of the embodiments of the present invention. It is, of course, possible for those skilled in the art to change and modify the embodiment shown in FIG. 2 through FIG. 8 so that the optical measuring device is hand-movable. A modification of the above-described embodiment shown in FIG. 2 through FIG. 8 is illustrated in FIG. 16 through FIG. 19. FIGS. 16 through 19 show a measuring optical system 8', a measuring light projecting optical system 9', a measuring light receiving optical system 10', and an axes alignment detecting optical system 50, respectively.

Figure 16:
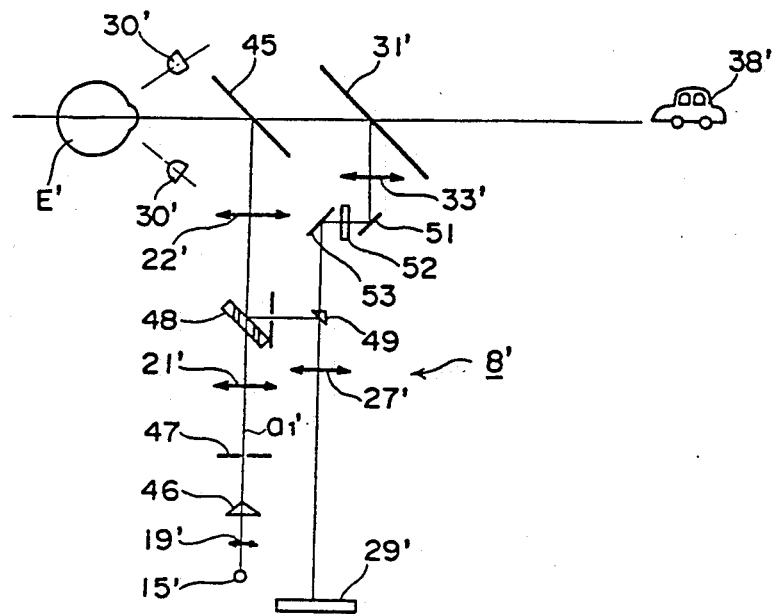
FIG. 16 is a view showing a measuring light optical system of a modified embodiment.
Figure 17:
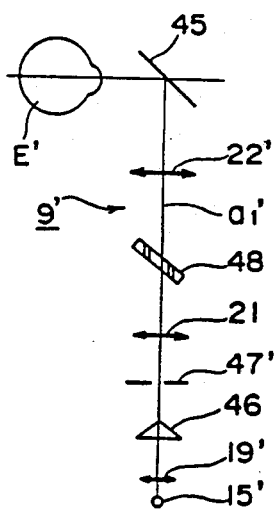
FIG. 17 is a measuring light projecting optical system composing the measuring light optical system shown in FIG. 16.
Figure 18:
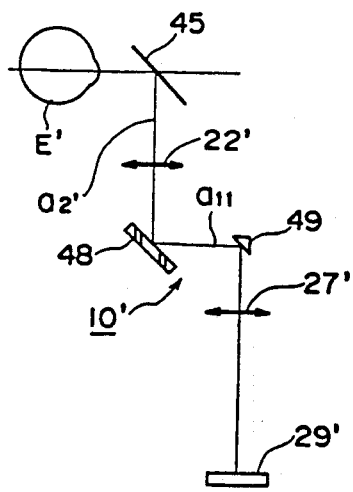
FIG. 18 is a measuring light receiving optical system composing the measuring light optical system shown in FIG. 16.
Figure 19:
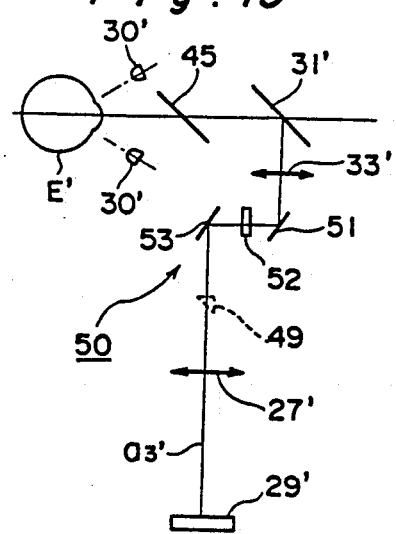
FIG. 19 is an axes-aligned state detecting optical system composing the measuring light optical system shown in FIG. 16.

Describing the measuring light projecting optical system 9' with reference to FIGS. 16 and 17, a half mirror 45 is used instead of the half prism 17. A measuring light emitted by an infrared ray projecting light source 15' travels rectilinearly to the half mirror 45, along an optical axis $a_1'$, by which the light is reflected at an angle of 90°. The light enters into an eye (E') disposed on the optical axis $a_1'$. The following are arranged on the optical axis $a_1'$ in the order of a collimator lens 19', a quadrangular pyramid 46, a diaphragm 47, a light projecting relay lens 21', a four-opening mirror 48, and an eyepiece 22' as viewed from the light source 15' toward the half mirror 45. The quadrangular pyramid 46 divides the infrared ray which has passed through the collimator lens 19' into four light beams which are spaced from each other at an angular interval of 90° in the periphery of the optical axis $a_1'$ so that the pattern consisting of four spots is formed. The four light beams which have passed through the quadrangular pyramid 46 and the diaphragm 47 corresponding to the focal point of the relay lens 21' are incident on the relay lens 21', thus forming four spots in parallel with the optical axis $a_1$. The four-opening mirror 48 reflects a light reflected from the retina, namely, a measuring light at an angle of 90° so that the measuring light is received by the measuring light receiving optical system 10'. The four-opening mirror 48 forms 45° with the optical axis $a_1'$ and is provided with small openings in the portions corresponding to the optical paths of the spot pattern so as not to intercept the four light beams of the spot pattern. Thus, the measuring light which has passed through the openings of the four-opening mirror 48 is divided into four light beams of the four-spot pattern. The four light beams are incident on the eyepiece 22', then reflected by the half mirror 45 at an angle of 45°, thus entering into the eye (E').

In the measuring light receiving optical system 10', the measuring light travels back from the eye (E') to the four-opening mirror 48, along the optical path of the light projecting optical system 9', by which the measuring light is reflected at an angle of 90°. A micromirror 49 having a face parallel with the four-opening mirror 48 is disposed on the optical axis $a_2'$ of the measuring light reflected by the four-opening mirror 48. The measuring light is reflected downward at an angle of 90°. An image forming lens 27' and a light receiving sensor 29' are arranged below the micromirror 49 along the optical axis $a_2'$.

In the axes alignment detecting optical system 50, the illuminated light which has been reflected from the cornea and partially passed through the half mirror is reflected downward at an angle of 90° by a dichroic mirror 31', thus passing through a monitor relay lens 33'. A first mirror 51 which forms 45° with the optical axis of the illuminated is arranged along the optical axis $a_3$ below the monitor relay lens 33'. A transparent reticle plate 52 carrying a reticle pattern is disposed on the optical path of the illuminated light. The reticle plate 52 and the eye (E') are conjugate to each other with respect to the monitor relay lens 33'. The light which has passed through the first mirror 51 and the reticle plate 52 is incident on a second mirror 53, which forms 45° with the optical axis, by which the light is reflected downward at an angle of 90°. The optical path of the measuring light receiving optical system 10' is the same as than of the axes alignment detecting optical system 50 below the micromirror 49, i.e., both optical system shaving the image forming lens 27' and the light receiving sensor 29' in common. Accordingly, the axes alignment detecting optical system 50 has a construction in which the monitoring reticle optical system is incorporated in the monitoring camera optical system. The micromirror 49 of the axes alignment detecting optical system 50 is so small that the light passes in the periphery thereof, thus causing no problems in measuring the refractive power of eye (E').

According to the construction and operation of the above-described embodiment and the modified embodiment, as shown in FIG. 20, the main body 2 is mounted on a table or the like and an examiner locates the hand-movable optical measuring device 1 in hand toward a patient so that a patient looks the optical pattern 38 from the window thereof as though it is 3~5 m far from the patient's eye. When the optical axes-aligned and in-focus states are obtained during the fine adjustment of the inclination and position of the optical measuring device 1 while the examiner is watching the monitor 4, the microcomputer 5 contained in the main body 2 calculates the data inputted thereto, thus the monitor 4 displaying the calculation performed by the microcomputer 5. Therefore, the period of time required for the examination of the eye is reduced and the location and the inclination of the optical measuring device 1 can be adjusted to the posture of the patient. As such, the examiner can easily measure the refractive powers of the patient's eyes and the patient can undergo the examination with comfort.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. An apparatus for measuring the refractive power of an eye having an optical measuring device provided with a measuring optical system for measuring the refractive power of the eye and a main body for calculating the refractive power of the eye based on data transmitted thereto from said optical measuring device, wherein said optical measuring device is separated from said main body so as to be hand-movable with respect to said main body and includes:
    a measuring light projecting optical system for projecting a measuring light so as to project an optical pattern on the retina of the eye;
    a measuring light receiving optical system in which a light reflected from the pattern projected on the retina of the eye is received by a light receiving sensor;
    a visual target optical system for allowing the eye to watch a visual target disposed at a far point with respect to the eye, and
    an optical system including an illuminating optical system and an optical axes-aligned state detecting optical system which comprises an illuminating light source for illuminating the eye so that an illuminated pattern image reflected from the cornea of the eye is used as an optical axes-aligned state detecting light, the optical axes-aligned state detecting optical system allowing said light receiving sensor to receive a light reflected form the eye;
    a monitor means being provided at least in one of said optical measuring device and said main body so as to display the eye based on an image signal transmitted thereto from said light receiving sensor and to display an optical axes-aligned state detecting reticle pattern on the screen thereof, said main body comprising:
        an image processing device for detecting coordinates of the illuminated pattern image and the projected pattern image with respect to an optical axis of said measuring light receiving optical system and luminances of the illuminated and projected pattern images based on image signals transmitted thereto from said light receiving sensor;
        optical axes-aligned state detecting means for detecting the axes-aligned state of said measuring optical system with respect to the eye based on the coordinate data of the illuminated pattern image transmitted thereto from said image processing device;
        in-focus state detecting means for detecting the focused state of said measuring optical system with respect to the eye based on luminance data of the illuminated pattern image transmitted thereto from said image processing device;
        measurement starting means for allowing said measuring light projecting optical system to project a measuring light based on focusing and axes-aligning information transmitted thereto from said optical axes-aligned state detecting means and said in-focus state detecting means, and
        calculating means for calculating the refractive power of the eye based on the coordinate data of the illuminated pattern image transmitted thereto from said image processing device.

2. An apparatus as claimed in claim 1, wherein the light source of said illuminating optical system and said axes-aligned state detecting optical system comprises a plurality of spot light sources disposed circumferentially of theoptical axis of said measuring light projecting optical system and symmetrically with each other with respect thereto.

3. An apparatus as claimed in claim 2, wherein a plurality of said spot light sources are supported by a disk member mounted on the housing of said optical measuring device so as to be rotatable about said optical axis and a weight for maintaining the posture of said disk member is fixed to said disk member at a predetermined position thereof so that predetermined spot light sources continually take predetermined positions;
    said main body comprises;
    means for selectively turning on said predetermined light sources; and
    means for detecting the posture of said optical measuring device with respect to the eye based on the coordinates of the illuminated spot images corresponding to said predetermined light sources detected by said image processing device.

4. An apparatus as claimed in claim 3, wherein said predetermined light source comprises a pair of spots symmetrical with respect to said axis of said measuring light projecting optical system.

5. An apparatus as claimed in claim 1, wherein said image processing device comprises means for detecting the high frequency component of the illuminated pattern image;

said in-focus state detecting means includes means for comparing the high frequency component of the illuminated pattern image with a reference value and deciding that an in-focus state is obtained when the high frequency component is greater than the reference value.

6. An apparatus for measuring the refractive power of eye having an optical measuring device provided with a measuring optical system for measuring the refractive power of eye and a main body for calculating the refractive power of eye based on data transmitted thereto from said optical measuring device, wherein said measuring optical system comprises;

a measuring light projecting optical system for projecting a measuring light so as to project a pattern on the retina of the eye, a measuring light receiving optical system in which a light reflected from the pattern projected on the retina of the eye is received by a light receiving sensor, a visual target optical system for allowing the eye to watch a visual target disposed at a far point with respect to the eye, and an optical system including an illuminating optical system and an optical axes-aligned state detecting optical system which comprises an illuminating light source for illuminating the eye so that an illuminated pattern image reflected from the cornea of the eye is used as an optical axes-aligned state detecting light, the optical axes-alinged state detecting optical system allowing said light receiving sensor to receive a light reflected from the eye, a monitor means being provided at least in one of said optical measuring device and said main body so as to display the eye based on an image signal transmitted thereto from said light receiving sensor and to display an optical axes-aligned state detecting reticle pattern on the screen thereof, said main body comprises;

means for detecting in-focus and optical axes-aligned states of the measuring optical system with respect to the eye based on the image signal transmitted thereto from said light receiving sensor, measurement starting means for allowing the measuring light projecting system to project a measuring light based on the focusing and axes-aligning information transmitted thereto from said means for detecting focusing and optical axes-aligned states, and a calculating means for calculating the refractive power of eye based on the information of the projected pattern image transmitted thereto from said light receiving sensor.

7. An apparatus for measuring the refractive power of eye having an optical measuring device provided with a measuring optical system for measuring the refractive power of eye and a main body for calculating the refractive power of eye based on data transmitted thereto from said optical measuring device, wherein said measuring optical system comprises;

a measuring light projecting optical system for projecting a measuring light so as to project a pattern on the retina of the eye, a measuring light receiving optical system in which a light reflected from the pattern projected on the retina of the eye is received by a light receiving sensor, a visual target optical system for allowing the eye to watch a visual target disposed at a far point with respect to the eye, an illuminating optical system for illuminating the eye so that a light reflected from the eye is received by said light receiving sensor, and an optical axis-aligned state detecting system which has a light source and allows said light receiving sensor to receive the light reflected from the eye, monitor means being provided at least in one of said optical measuring device and said main body so as to display the eye based on an image signal transmitted thereto from said light receiving sensor and to display an optical axes-aligned state detecting reticle pattern on the screen thereof, said main body comprises;

means for detecting in-focus and optical axes-aligned states of the measuring optical system with respect to the eye based on the image signal transmitted thereto from said light receiving sensor, measurement starting means for allowing the measuring light projecting system to project a measuring light based on the focusing and axes-aligning information transmitted thereto from said means for detecting focusing and optical axes-aligned states, and a calculating means for calculating the refractive power of eye based on the information of the projected pattern image transmitted thereto from said light receiving sensor.

8. An apparatus for measuring the refractive power of eye having a optical measuring device provided with a measuring optical system for measuring the refractive power of eye and a main body for calculating the refractive power of eye based on data transmitted thereto from said optical measuring device, wherein measuring optical system comprises;

a measuring light projecting optical system for projecting a measuring light so as to project an optical pattern on the retina of the eye, a measuring light receiving optical system in which a light reflected from the pattern projected on the retina of the eye is received by a light receiving sensor, an optical system including an illuminating optical system and an optical axes-aligned state detecting optical system which comprises an illuminating light source for illuminating the eye so that an illuminated pattern image reflected from the cornea of the eye is used as an optical axes-aligned state detecting light, and the optical axes-alinged state detecting optical system allowing said light receiving sensor to receive a light reflected from the eye, said main body comprises;

an image processing device for detecting coordinates of the illuminated pattern image and the projected pattern image with respect to an optical axis of said measuring light receiving optical system and luminances of the illuminated and projected pattern images based on image signals transmitted thereto from said light receiving sensor, optical axes-aligned state detecting means for detecting the axes-aligned stat of said measuring optical system with respect to the eye based on the coordinate data of the illuminated pattern image transmitted thereto from said image processing device, in-focus state detecting means for detecting focused state of said measuring optical system with respect to the eye based on luminance data of the illuminated pattern image transmitted thereto from said image processing device, measurement starting means for allowing said measuring light projecting optical system to project a measuring light based o focusing and axes-aligning information transmitted thereto from said optical axes-aligned state detecting means and said in-focus state detecting means, and calculating means for calculating the refractive power of eye based on the coordinate data of the illuminated pattern image transmitted thereto from said image processing device.

9. An apparatus for measuring the refractive power of eye having an optical measuring device provided with a measuring optical system for measuring the refractive power of eye and a main body for calculating the refractive power of eye based on data transmitted thereto from said optical measuring device, wherein said measuring optical system comprises;

a measuring light projecting optical system for projecting a measuring light so as to project a pattern on the retina of the eye, a measuring light receiving optical system in which a light reflected from the pattern projected on the retina of the eye is received by a light receiving sensor, an illuminating optical system for illuminating the eye so that a light reflected from the eye is received by said light receiving sensor, and an optical axis-aligned state detecting system which has a light source and allows said light receiving sensor to receive the light reflected from the eye, said main body comprises;

means for detecting in-focus and optical axes-aligned states of the measuring optical system with respect to the eye based on the image signal transmitted thereto from said light receiving sensor, measurement starting means for allowing the measuring light projecting system to project a measuring light based on the focusing and axes-aligning information transmitted thereto from said means for detecting focusing and optical axes-aligned states, and a calculating means for calculating the refractive power of eye based on the information of the projected pattern image transmitted thereto from said light receiving sensor.

10. An apparatus for measuring the refractive power of an eye having an optical measuring device provided with a measuring optical system for measuring the refractive power of eye and a main body for calculating the refractive power of eye based on data transmitted thereto from said optical measuring device, wherein said measuring optical system comprises;

an optical system including an illuminating optical system and an optical axes-aligned state detecting optical system which comprises an illuminating light source for illuminating the eye so that an illuminated pattern image reflected from the cornea of the eye is used as an optical axes-aligned state detecting light, the optical axes-aligned state detecting optical system allowing said light receiving sensor to receive a light reflected from the eye, said illuminating light source comprising a plurality of spot patterns sources disposed circumferentially of the optical axis of a measuring light projecting optical system and symmetrically with each other with respect thereto;

said main body includes means for detecting in-focus and optical axes-aligned states of said measuring optical system based on an image signal transmitted thereto from said light receiving sensor.

11. An apparatus for measuring the refractive power of an eye having an optical measuring device provided with a measuring optical system for measuring the refractive power of eye and a main body for calculating the refractive power of eye based on data transmitted thereto from said optical measuring device, wherein said measuring optical system comprises;

a measuring light projecting optical system for projecting a measuring light so as to project a pattern on the retina of the eye, and a measuring light receiving optical system for allowing a light receiving sensor to receive a light reflected from the pattern projected on the retina of the eye, said projective pattern of the measuring light including two spot lights spaced from each other by 90° with respect to and in the circumference of the optical axis of said measuring light projecting optical system, said measuring light receiving optical system including on the optical axis thereof an eyepiece which condenses lights reflected from spot images formed on the retina of the eye, a diaphragm which allows the passages of the light beams which have been reflected from the retina and passed through said eyepiece, an image forming lens which allows the passages of the light beams which have passed through said diaphragm, and said light receiving sensor which receives the lights of the spot images formed by the image forming lens, said diaphragm being substantially conjugate to the cornea of the eye with respect to the eyepiece and having an aperture small enough to select a light beam from light beams reflected from spot images formed on the retina so as to allow the passage of said light beam which passes the point at which the cornea and the optical axis of said measuring light receiving optical system cross each other.

12. An apparatus for measuring the refractive power of an eye having an optical measuring device provided with a measuring optical system for measuring the refractive power of eye and a main body for calculating the refractive power of eye based on data transmitted thereto from said optical measuring device, wherein said measuring optical system comprises, a measuring light projecting optical system for projecting a measuring light so as to project a pattern on the retina of the eye and a measuring light receiving optical system for allowing a light receiving sensor to receive a light reflected from the pattern projected on the retina of the eye;

said projective pattern of the measuring light including four spots spaced from each other by 90° with respect to and in the circumference of the optical axis of said measuring light projecting optical system;

said measuring light receiving optical system including on the optical axis $a_1$ thereof an eyepiece which condenses lights reflected from spot images formed on the retina of the eye, an image forming lens which allows the passage of the light beams which have been reflected from the spot images formed on the retina of the eye and passed through said eyepiece, and said light receiving sensor which receives the lights of the spot images formed by the image forming lens;

said main body comprises;

first calculating means for calculating, based on position data of each pair of spot images detected by the light receiving sensor, the height ($h_0$) of a pair of spot images corresponding to the height (h) of points (Q) and (Q') of the spots projected on the retina of the eye by said measuring light projecting optical system in which two spot images of each pair received by said light receiving sensor are symmetrical with respect to the optical axis of said measuring light receiving optical system and the height (h) of said spot images (Q) and (Q') correspond to the distance from the optical axis $a_E$ of the eye, and second calculating means for calculating the refractive power of eye based on said height ($h_0$).

13. An apparatus as claimed in claim 12, wherein said first calculating means calculates the first height ($h_0'$) corresponding to one of said each spot images and the second height ($h_0''$) corresponding to the other thereof per each pair with respect to the optical axis of said measuring light receiving optical system detected by the light receiving sensor, and according to an equation of $$h_0 = \frac{h_0' - h_0''}{2}$$

calculates the height ($h_0$) of said two spot images corresponding to the height (h) of said points (Q) and (Q') of the lights on the retina of the eye projected by said measuring light projecting optical system in which the height (h) of said points (Q) and (Q') are the distance from the optical axis of said measuring light receiving optical system.

14. An apparatus as claimed in claim 12, wherein said measuring light receiving optical system further includes a diaphragm between said eyepiece and said image forming lens, said diaphragm being conjugate to the cornea of the eye with respect to said eyepiece and has an aperture whose diameter is great enough to allow the passage therethrough a light beam having an amount necessary for said light receiving sensor to detect a spot image formed on said light receiving sensor.

15. An apparatus for measuring the refractive power of eye having an optical measuring device provided with a measuring optical system for measuring the refractive power of eye and a main body for calculating the refractive power of eye based on data transmitted thereto from said optical measuring device, wherein said measuring optical system comprises;

a measuring light projecting optical system for projecting a measuring light so as to project a pattern on the retina of the eye, and a measuring light receiving optical system for receiving a light reflected from the pattern projected on the retina of the eye, said projected pattern of the measuring light including four spots spaced from each other by 90° with respect to and in the circumference of the optical axis of said measuring light projecting optical system, said main body includes;

a deciding means for deciding the error amount between the optical axis of said measuring light optical system and the optical axis of the eye based on the positions of the images of four patterns relative to the optical axis of said measuring light receiving optical system, a comparing means for comparing said error amount with a reference value, and a means for performing an error processing by deciding that an error has occurred when said error amount is greater than said reference value.

16. In an apparatus for measuring the refractive power of an eye having an optical measuring device provided with a measuring optical system with an optical axis for measuring the refractive power of the eye and calculation means for calculating the refractive power of the eye based on data transmitted thereto from said optical measuring device, the improvement comprising:

a first housing member for mounting the optical measuring device, the housing member including a handle portion for holding by a single hand of an operator, the optical measuring device further including light projection means for projection of light, means for detecting the alignment of an optical axis of the eye with the optical axis and means for having the calculation means effect its calculation when the alignment is detected;

a second housing member for mounting the calculation means including a display for disclosing the calculated refractive power, and means for interconnecting the first and second housing member to permit the first housing member to be relatively moved in a hand-held state while the second housing member remains stationary.

* * * * *